United States Patent
Christie et al.

(10) Patent No.: US 7,819,028 B2
(45) Date of Patent: Oct. 26, 2010

(54) ENVIRONMENTAL CONTAMINANT SAMPLING AND ANALYSIS

(75) Inventors: Ian McIntyre Christie, Portsmouth (GB); Anthony Charles Downer, Portsmouth (GB); Ian Paul Andrews, Portsmouth (GB); Anthony Cooke, Portsmouth (GB)

(73) Assignee: Life Safety Distribution AG, Uster (CH)

( * ) Notice: Subject to any disclaimer, the term of this patent is extended or adjusted under 35 U.S.C. 154(b) by 755 days.

(21) Appl. No.: 11/663,700

(22) PCT Filed: Sep. 22, 2005

(86) PCT No.: PCT/GB2005/003637

§ 371 (c)(1),
(2), (4) Date: Jun. 27, 2007

(87) PCT Pub. No.: WO2006/032881

PCT Pub. Date: Mar. 30, 2006

(65) Prior Publication Data

US 2008/0078256 A1    Apr. 3, 2008

(30) Foreign Application Priority Data

Sep. 24, 2004  (GB) .................................. 0421352.6

(51) Int. Cl.
    *G01N 1/00*    (2006.01)
(52) U.S. Cl. .................................................. 73/863.23
(58) Field of Classification Search ........................ None
    See application file for complete search history.

(56) References Cited

U.S. PATENT DOCUMENTS

| 4,426,214 A | * | 1/1984 | Vandrish .................... 55/511 |
| 4,568,520 A | * | 2/1986 | Ackermann et al. .......... 422/66 |
| 4,675,034 A | | 6/1987 | Lynch et al. |
| 4,795,612 A | * | 1/1989 | Keller ...................... 422/64 |
| 5,817,522 A | | 10/1998 | Goodman et al. |
| 6,023,981 A | * | 2/2000 | Phillips et al. .......... 73/863.23 |
| 6,101,886 A | | 8/2000 | Brenizer et al. |
| 6,228,657 B1 | | 5/2001 | Genovese et al. |
| 6,766,817 B2 | | 7/2004 | da Silva |
| 6,918,404 B2 | | 7/2005 | Dias da Silva |

(Continued)

FOREIGN PATENT DOCUMENTS

EP    0 447 158 A1    9/1991

(Continued)

OTHER PUBLICATIONS

E. Dunn and R. Brotherton, "The Use of NN-Dimethylcasein in the Determination of Proteolytic Enzymes in Washing Products and Airborne Dust Samples", Procter & Gamble Limited, Analyst, Feb. 1971, vol. 96, pp. 159-163.

*Primary Examiner*—Robert R Raevis
(74) *Attorney, Agent, or Firm*—Husch Blackwell LLP Welsh Katz

(57) ABSTRACT

A sampling and analysis device comprises a housing, a sampling region and an analysis region being defined within the housing. The housing has at least one aperture to allow fluid ingress to and egress from the sampling region. A filter is disposed within the housing, and is movable inside the housing between a sampling position, located in the sampling region, and an analysis position, located in the analysis region.

53 Claims, 17 Drawing Sheets

U.S. PATENT DOCUMENTS

| | | |
|---|---|---|
| 7,066,586 B2 | 6/2006 | da Silva |
| 7,285,255 B2 | 10/2007 | Kadlec et al. |
| 2004/0035186 A1 | 2/2004 | Allen et al. |
| 2007/0277626 A1 * | 12/2007 | Saitoh et al. ............. 73/863.23 |

FOREIGN PATENT DOCUMENTS

| | | |
|---|---|---|
| GB | 2 261 949 A | 6/1993 |
| GB | 2 351 560 A | 3/2001 |
| WO | WO 03/016871 A1 | 2/2003 |

* cited by examiner

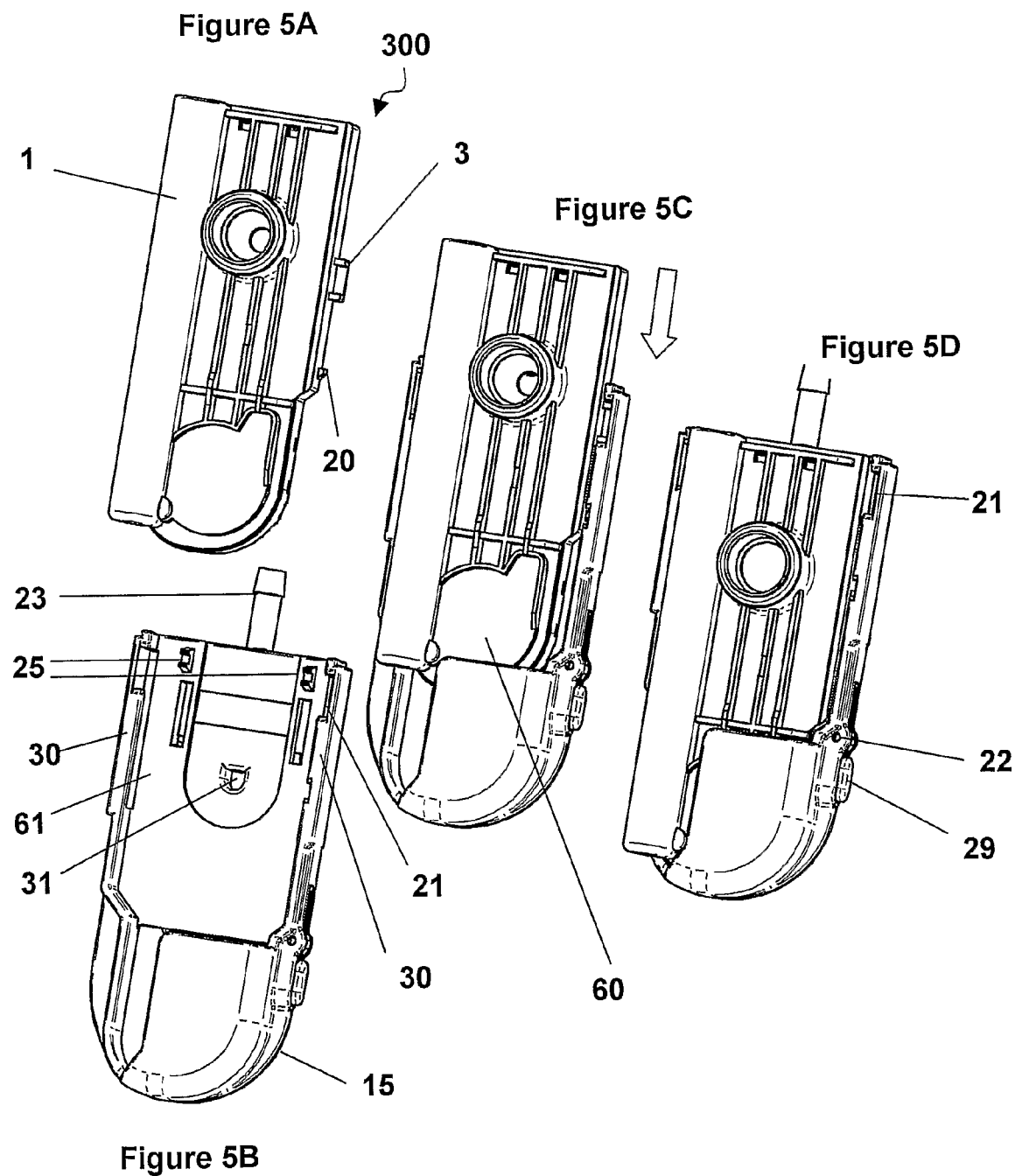

ENVIRONMENTAL CONTAMINANT SAMPLING AND ANALYSIS

This invention relates to a device, assembly and system for carrying out sampling and analysis of contaminants carried by a fluid. The invention further relates to a method of carrying out sampling and analysis.

There are many situations, both domestic and industrial, in which it is important to be able to detect and measure contaminants which may be present in the environment. Of particular concern are contaminants which may be easily carried by gas or liquid and thus transported or otherwise dispersed rather than being easily contained. For example, certain airborne particles may be inhaled by people living or working in the area, leading to injury or disease. A particular example are enzymes, of which different types come from a variety of sources and can result in allergies and other health risks.

Protease enzymes break up protein. Some are found in the faeces of dust mites, and cause dust allergies in the domestic environment. Commercial systems exist for the measurement of such enzymes, for example those disclosed in GB2351560 and WO03016871. In these systems, a cartridge containing a filter is attached to the end of a hand held vacuum cleaner and dust is sucked off surfaces for a predetermined time. The cartridge is then removed and placed on a flat surface at room temperature. Reagents (liquid buffer and detergent) contained within a blister section of the cartridge are released by breaking a seal, thereby allowing liquid onto the filter and a contacting porous wick on which are immobilised a "substrate" and colour developer in dried form. In this context, the "substrate" is defined as the starting chemical or feedstock in an enzyme-catalysed reaction.

The reagents pick up and/or dissolve enzyme and carry it along the wick where they catalyse the break up of the substrate to give a yellow product from the enzyme reaction. The yellow colouration developed by this primary reaction is difficult to observe on a white wick, so the reagent flow is arranged to continue along the wick to a second dried reagent that reacts with it to give a purple colour. This may be readily inspected with the naked eye and high, medium, low levels estimated from comparison with a chart.

Subtilisins are another type of protease derived from bacteria and this group of enzymes is used in biological washing powder to digest protein stains. Due to the possible health implications (e.g. the risk of developing asthma) for workers operating for extended periods in environments where significant quantities of these enzymes may be present in inhaled air, there is a requirement to monitor the levels of such substances in workplace air where detergents are manufactured. However, the relatively crude measurement which may be derived using the method outlined above is inadequate for long term workplace monitoring and a much more robust, quantitative technique is required.

Current methods for the industrial monitoring of subtilisins in detergent are typically based on methods such as those outlined in "The use of NN-dimethylcasein in the determination of proteolytic enzymes in washing products and airborne dust samples" (E Dunn and R Brotherton, Analyst 96 159-163 February 1971). Although many of the details are not disclosed, such systems normally employ personal sampling pumps (with inlets attached to the lapel of the user, adjacent to the breathing zone) which pull air through a 25 mm diameter filter at about 2 liters per minute as described in, for example, U.S. Pat. No. 4,675,034. Alternatively, "Galley sampling" may be used, in which a much larger filter (typically 150 mm diameter) is fed at over 100 liters per minute in a mobile unit whose location can be chosen to provide area monitoring appropriate to the operational requirements.

In either case, the sampling system is designed to ensure that the filter medium reproducibly absorbs any enzyme present in the atmosphere; it will also of course simultaneously absorb background dust. To process the filter, it must be removed from the sampling head (in which it is usually a replaceable element) and transported to a laboratory or other remote location where subsequent analysis takes place.

The enzyme is extracted from the filter by dispersing in liquid. This takes several minutes and the filter often tends to break up during the process, especially if stirring or agitation is employed to improve the extraction. Consequently, it is necessary to filter the liquid containing the enzyme to remove this debris before subsequent analysis can take place. However, this also means that any enzyme still adhering to the filter particles will be lost from the sample before the chemical reaction is run, hence compromising the net sensitivity of the system.

A chemical reaction is then performed to determine the concentration of enzyme in the filtrate. Typically, a protein (NN-dimethylcasein, DMC) is broken up by the enzyme to release fragments with free amine groups. These free amines react with 2,4,6 Trinitrobenzenesulphonic acid (TNBS/TN-BSA) to produce a yellow colour which can be determined with adequate precision by spectrophotometric analysis at 425 nm. Incubation of the mixture for some minutes at approximately 40 to 50° C. may also be necessary to drive the reaction satisfactorily.

Whilst this system may be capable of providing adequate precision (the spectrophotometer may be calibrated by the use of standard colour solutions), it is clear that the process requires considerable operator skill and training in order to provide reproducible data. There are numerous points at which handling and transport of the filter are required and each of these operations carries with it a significant risk of contamination and/or loss of enzyme on the filter. The detection limit varies according to the enzyme in question, but a typical example (Savinase) using a conventional system gives a detection limit of a few ng per ml (volume values refer to the enzyme when resuspended in fluid). Industrial personal monitoring systems however demand high sensitivity and ideally would require enzyme mass resolutions of approximately 1 ng.

It should be noted that the term "sampling" is used herein, as in the examples given above, to refer to the collection of contaminants (or other such analytes) directly from the fluid medium under investigation. This is to be contrasted with alternative techniques of introducing an analyte into a device, such as (i) deposition or application of a (generally liquid) substance into a region of a device (for example, by pipette), and (ii) specific binding techniques, in which chemical reagents are used to selectively collect certain components from the medium under investigation. "Sampling", on the other hand, generally involves the filtering of analyte entities (e.g. particles, molecules or droplets) from a background fluid without "specific" differentiation of a target analyte.

U.S. Pat. No. 5,817,522 discloses a self-contained assay device for analysing a sample via a sequence of reactions which take place in a series of chambers through which the sample is rotated. Each chamber contains a capsule which is broken to release a reagent or a wash solution. The sample is introduced to the device by depositing a precollected specimen solution through an opening in the device onto a plate at a predetermined position which is provided with specific binders. Target analytes selectively bind to the surface and any excess liquid is absorbed by a blotter member. This apparatus is not suitable for collecting a sample from a flow of fluid (gaseous or liquid). Moreover, the amount of sample collected is determined by the amount of binder provided on the plate and thus does not allow the user to make quantitative measurements of the amount of target analyte in the fluid.

Similarly, GB-A-2261949 discloses an apparatus in which a liquid sample (for example a solution of a gaseous specimen) is applied to a carrier belt by means of an immunobinding event. The sample reacts with reagents which may be pre-applied to the carrier belt, mixed into the sample solution or applied to the belt after the sample. The sample is moved on to a separate detection assembly where the result of the reaction is detected, for example by means of fluorescence. This apparatus presents similar drawbacks to those described above in relation to U.S. Pat. No. 5,817,522.

EP-A-0447158 discloses a detector for explosive or narcotic substances in which air is drawn through a cyclone to deposit a sample on a glass fibre frit, positioned below. Each frit comprises a set of resistive heating wires covered with glass fibre, and is supported on a rotary table which moves the frit from the sample collection position into a separate ion mobility spectrometer ("IMS"). In this position, the frit is heated and particles of the collected samples are dispersed into the IMS chamber by passing a desorption gas through the frit. A reagent gas may also be introduced. The spectrometer then analyses the vaporised material to determine its composition. Like the known systems described above, this system suffers from the problem that the sample generally does not desorb completely from the frit and thus it is not possible to take accurate quantitative measurements.

U.S. Pat. No. 6,101,886 discloses a sample concentrator for collecting a particulate sample from the atmosphere and preparing it for analysis. However the apparatus does not provide any means for carrying out any subsequent analysis or detection processes.

Advantages achieved by the present invention include the provision of an improved system and method for the monitoring of such contaminants, especially in the industrial workplace, with high sensitivity and quantitative, accurate results. Further, the sampling and analysis procedure is simplified so that results may be obtained quickly and by unskilled personnel.

In accordance with a first aspect of the present invention, a sampling and analysis device comprises a housing, a sampling region and an analysis region being defined within the housing, the housing having at least one aperture to allow fluid ingress to and egress from the sampling region and a filter disposed within the housing, wherein the filter is movable inside the housing between a sampling position, located in the sampling region, and an analysis position, located in the analysis region.

This arrangement makes it possible to carry out all the sampling and analysis steps inside one housing or cartridge. A sample of the contaminant carried by the fluid is obtained by exposing the filter to the fluid in the sampling region of the device. The contaminant, which may comprise solid particles or liquid aerosol particles, for example, is adsorbed on to the filter which can then be moved away from the flow of fluid and into the analysis region. Depending on the particular contaminant to be detected and the chemistries used, a reaction involving the collected sample can be initiated or promoted in a number of ways as will be discussed below. The reaction can be monitored and information about the contaminant obtained. By carrying out all these steps in one cartridge, no handling of the filter and the sample carried thereupon is required between sampling and analysis. The filter remains inside the cartridge throughout the sampling and analysis steps and is never removed. The reaction takes place inside the cartridge, thus containing all reagents and waste products which could, potentially, be harmful. Hence the cartridge is suitable for handling by unskilled persons. Moreover, the filter remains in the analysis region throughout the analysis process and is not disposed of. The fact that there is no contamination or loss of the sample leads to improved accuracy and more sensitive results since the whole collected sample can take part in the reaction.

The reaction may be promoted by a variety of means. For example, the filter could be impregnated with a reagent and its exposure to the contaminant sample could start the reaction without any additional actuation step. In other cases, the reaction could be initiated by heating the collected sample on the filter or by irradiation. Heating or irradiation apparatus could be provided either integrally in the device or externally. In a preferred embodiment however, the device further comprises means for introducing a reagent to the analysis region. In this way, liquid or gel (for example) reagents can be added at the desired time, making a wide variety of reactions possible.

Advantageously, the aperture in the sampling region comprises an inlet aperture through which fluid enters the device, and the device further comprises an outlet aperture in the sampling region through which fluid exits the device, the filter being located between the inlet and outlet apertures when it is in the sampling position, so as to collect contaminants from fluid flowing between the inlet and outlet apertures. As such, the device is particularly well disposed to sample contaminants by filtering. This makes the device particularly well adapted to collect samples directly from the substance (e.g. an atmosphere or liquid) under investigation, without the need for a sample preparation step.

Preferably, the device further comprises first sealing means which isolate the analysis region from the sampling region at least when the filter is at the analysis position. The analysis region can be sealed from the rest of the housing, retaining the reagents (if present) and thus avoiding potential leakage should the cartridge be inverted or mishandled.

Preferably, the device further defines a safe region within the housing, the filter being further movable between the sampling or analysis positions and a safe position, located in the safe region, the filter being sealed from at least the sampling region when the filter is at the safe position.

The safe region provides a convenient way to store the filter away from the external environment and from any reagents or other reaction-activating means. In the safe position, the filter is not in fluid communication with the inlet or outlet apertures, and so is protected from contamination while the device is not in use. Sealing could be achieved using the first sealing means or some additional seal. Alternatively, it would be possible to provide the apertures with removable covers so that they could be sealed until the device was ready for use.

Preferably, when the filter is at the safe position, it is further sealed from the analysis region. This avoids contact between the filter and the reagents and thus prevents premature reactions taking place.

Advantageously, the filter is movable along a rectilinear path inside the housing. This allows its movement to be simply and economically controlled by straightforward means (e.g. by sliding) and places the fewest constraints on the shape and size of the device components.

Conveniently, the filter is mounted on a filter support, the filter support shaped so as to allow fluid to pass through the filter, in use. The filter support, or "shuttle", provides reinforcement for the filter (which may be fragile) and may conveniently be used to support the filter as it is moved between the various positions inside the housing. Conveniently, the first sealing means comprise a seal provided between the filter support and the housing. This is preferably mounted to the filter support, and may, for example, be in the form of an elastomeric ring extending around the filter support. Since the seal is attached to the filter support, it moves with the filter. When the filter is at the analysis position, the seal acts to isolate the analysis region from the rest of the device, and when the filter is at the safe position, the seal isolates the safe region from the sampling region. Alternatively, a plurality of seals could be mounted to the interior of the housing in order to carry out these functions.

Preferably, the device further comprises second sealing means which, when the filter is in the sampling position, confine fluid flow to a volume of the sampling region defined by the second sealing means. When the filter is in the safe position, the second sealing means isolate the filter from the rest of the device. The second sealing means assist in the sampling process and in protecting the filter from contamination when it is not in use. In the sampling position, the second sealing means direct the fluid flow through the filter so that the sample obtained is an accurate representation of the contaminant entering the device during the sampling time. Preferably, the second sealing means comprise a seal extending around the perimeter of the filter between the filter and the housing.

Preferably, the filter support and housing are slidably engaged. This enables the filter support to be moved easily from one position to another inside the housing, and could be achieved in a number of ways. For example, the filter support could be sized so as to fit slidably against the interior walls of the housing or the filter support could slidably couple to a rod or other feature on the interior surface of the housing. Conveniently, the housing is further provided with an elongate aperture and the filter support comprises a tab which extends toward the elongate aperture. The tab can be engaged by suitable apparatus extending through the aperture from outside the housing. This provides a convenient way of moving the filter and its support inside the housing without needing to open the housing. This arrangement is straightforward to manufacture and easy to operate since there are few moving parts, but alternatively, the filter could be equipped with a magnetic portion, and a second magnet used outside the housing to move the filter as required, or a motor could be provided to move the filter relative to the housing.

Preferably, the housing is further provided with an analysis actuator aperture positioned away from the analysis region. This allows for an additional method of moving the filter inside the housing. A suitable implement may be inserted through the aperture and used to apply force to the filter or filter support. Typically this technique could be used to move the filter into the analysis position.

Preferably, where the reaction is initiated by the introduction of a reagent, the means for introducing a reagent comprise a reservoir adapted to contain a reagent in use, a passage between the reservoir and the analysis region and apparatus for causing the reagent to flow into the analysis region. The reagents can be stored in the reservoir for as long as their shelf life permits before the device is used. The reservoir may be provided in the form of a barrel, which could itself be movably mounted to the housing. Preferably, the apparatus is a piston provided inside the reservoir. Like the filter support, this may be provided with means for operating it from outside the device, such as tabs which can cooperate with external actuators via apertures in the housing or by means of a magnetic arrangement. Alternatively, the means for introducing a reagent could comprise a cavity adapted to contain a reagent in use, the cavity having at least one wall in common with the analysis region, at least a portion of the wall being frangible. In this case, the frangible portion of the wall could be broken by the movement of the filter itself (or the filter support), or an additional component could be provided with which to open the cavity and release the reagent. For example, the cavity could be a blister section.

In addition, one or more dry reagents or substrates may be provided in the analysis region. Introduction of liquid or gel reagents dissolve the dried chemical to initiate a reaction. As previously indicated, the filter itself could also be impregnated with one or more chemicals.

Preferably, the housing is further provided with a window located in a wall of the analysis region. This allows for optical interrogation of the contents of the analysis region in order that the reaction occurring therein may be monitored by means of spectrophotometry. Typically, entrance and exit windows are provided to allow spectrophotometric analysis in the transmission mode. However other methods (e.g. fluorescence) may employ more windows, depending on the optical arrangement. The reaction could also be visualised on the filter itself, for example by illuminating the filter with UV light. Alternatively, the device could be provided with alternative means for monitoring the reaction, such as electrodes displaced in the analysis region for carrying out electrochemical monitoring techniques.

Preferably, the device further comprises a stirrer located in the analysis region. This component not only assists in detaching the contaminant sample from the filter material, but also improves mixing of the reagent and contaminant, assisting the reaction and improving the homogeneity of the reaction mixture throughout the analysis region, improving the accuracy of the measurement. Preferably, the stirrer is adapted to be remotely actuated from outside the device housing. Alternatively, the stirrer could be provided with a motor or other actuation means inside the housing. The stirrer could be positioned anywhere within the analysis region, but it is convenient to locate the stirrer in a plane substantially parallel to that of the filter, the stirrer being rotatable about an axis perpendicular to that plane. Especially where the filter is fragile, the stirrer is preferably spaced from the filter in use. This means that the stirrer can be positioned adjacent to the filter, effectively dispersing the contaminant sample without damaging the filter material itself.

In accordance with a second aspect of the present invention, a sampling and analysis assembly comprises a device in accordance with the first aspect of the present invention and a holster adapted to couple with the device. The holster provides convenient means for mounting and handling the device. Preferably, the holster comprises means for affixing the assembly to a user. This could be in the form of a clip, pin, belt or adhesive patch, for example, and conveniently allows the assembly to be attached to a user whilst he carries out his work. Preferably, the assembly is affixed to the user near to his breathing zone (for example on the lapel of his clothing), so that an accurate measurement of the contaminant he is likely to inhale may be obtained. Alternatively the device could be mounted on a stand or wall etc. in order to undertake static rather than personal monitoring.

Conveniently, the holster is provided with means for moving the filter inside the device housing. Preferably, the device is provided with a filter support as described above, slidably engaged with the housing, and the means for moving the filter provided on the holster comprise a protrusion which cooperates with the tab on the filter support so as to slide the filter support alongside the elongate aperture as the device and holster are moved relative to one another. Alternatively, if the filter support is provided with a magnetic portion, the holster could also be provided with a magnet which interacts with the magnetic filter support and causes it to move.

Preferably, the device includes a safe region as described above and the means for moving the filter provided on the holster move the filter from the safe position to the sampling position as the device and the holster are coupled together, and return the filter to the safe position as the device and the holster are uncoupled. This means that coupling of the device cartridge to the holster automatically moves the filter into the sampling position, exposing it to the test environment. When the device is removed from the holster, the filter is returned to the safe position and thus sealed from the environment. As such, movement of the shuttle to and from the sampling position happens automatically and is not a step for the user to remember.

In accordance with a third aspect of the present invention, a holster is provided, the holster being adapted to couple with a sampling and analysis device according to the first aspect of the present invention.

In accordance with a fourth aspect of the present invention, a sampling and analysis kit comprises an assembly according to the second aspect of the invention and a pump for drawing fluid through the assembly. Typically, the holster is provided with an outlet aligned with the apertures in the device housing and provided with a nozzle to which a pump may be attached. The pump may be attached via a hose for convenience. Typically, the pump is also carried by the user, attached for example to his belt.

In accordance with a fifth aspect of the present invention, an analyser is provided for monitoring conditions inside a sampling and analysis device in accordance with the first aspect of the present invention. Preferably, the analyser is adapted to couple with the device in use, and comprises means for moving the filter inside the device housing. Alternatively, a separate actuator component may be used to move the filter and actuate the reactants and the analyser used to monitor the resulting reaction.

By employing an analyser which is separate from, but interacts with, the sampling and analysis device, sampling operations can take place away from the analysis station—for example, in different geographical locations and/or at different times. Further, the samples collected in each device can be analysed in one or more analysers in any order, at any time without disturbing measurements taken by other devices.

Each collection and analysis event is typically "single-shot"—i.e. each device takes one sample only, which can then be analysed, and the device disposed of or refilled with a new filter and appropriate reagents. It should be noted that, in most embodiments, the sampling and analysis device itself has no "reader" function. Rather, it provides a container for a reaction to take place inside. The results of the reaction are assessed by the (separate) analyser. As such, it is possible to simultaneously analyse one sample in a first device, whilst collecting another using a second device.

Preferably, the device comprises a filter support slidably engaged with the housing as described above, and the means for moving the filter provided on the analyser comprise a shaft which can be inserted into the housing through the analysis actuation aperture to contact and apply a force to the filter support. Alternatively, as previously described, the filter support and analyser could each be provided with magnetic means for moving the filter inside the device housing. The analyser could be provided with a protrusion which cooperates with the tab on the filter support so as to slide the filter support alongside the elongate aperture as the device and analyser are moved relative to one another. Preferably, the device includes a safe region and the means for moving the filter provided on the analyser are adapted to move the filter from the safe position to the analysis position. This could be activated manually (i.e. when the analyser receives an instruction) or could be set to happen automatically once the device is properly mounted in the analyser, or when the lid of the analyser is shut, for example. Alternatively, if the analyser is provided with a protrusion for engaging the filter support, the filter could be slid into the analysis region by the action of coupling the device with the analyser.

Preferably, where the reaction is initiated by the addition of a reagent, the analyser further comprises a reagent actuator for operating the means for introducing a reagent to the analysis region of the device. For example, if the means for introducing the reagent comprise a reservoir and piston as previously described, the reagent actuator may mechanically couple with the piston so as to force the reagent into the analysis region as the actuator is moved. The reservoir itself could also be moved relative to the housing by the actuator. Typically, the reagent actuator comprises a first actuator rod which cooperates with the piston so as to force the reagent into the analysis region as the rod is moved relative to the device. The reagent actuator may further comprise a second actuator rod which cooperates with the reservoir. Alternatively, if the means for introducing the reagents comprise a frangible cavity as previously described, the filter or filter support may itself provide the reagent actuator. Where the reaction is initiated by other means, the analyser could house heating or irradiation elements, for example.

Conveniently, the device includes at least one window in the analysis region and the analyser is provided with means for optical interrogation of the contents of the analysis region. Alternatively the analyser could be provided with alternative monitoring means such as a circuit for taking electrochemical measurements.

Preferably, where the device includes a stirrer in the analysis region, the analyser further comprises a stirrer actuator for operating the stirrer. The stirrer actuator and stirrer may be magnetically coupled, for example. Conveniently, the analyser further comprises means for heating the analysis region of the device. Control means may also be provided to provide heating at a controlled rate to a predetermined temperature.

In accordance with a sixth aspect of the invention, an actuator is provided which is adapted to couple to a sampling and analysis device according to the first aspect of the invention, the actuator comprising means for moving the filter inside the device housing and a reagent actuator for operating the means for introducing reagent to the analysis region of the device.

In accordance with a seventh aspect of the present invention, a sampling and analysis system is provided which comprises at least one of a device according to the first aspect of the present invention, an assembly according to the second aspect of the present invention and a kit according to the fourth aspect of the present invention, and an analyser according to the fifth aspect of the present invention. The system may additionally comprise an actuator in accordance with the sixth aspect of the invention.

In accordance with an eighth aspect of the present invention, a method of sampling and analysing contaminants in a fluid comprises the steps of a) passing the fluid through a filter, located at a sampling position inside a housing, such that a sample of the contaminants remains on the filter, b) moving the filter to an analysis position located in an analysis region inside the housing, and in which a reaction occurs involving at least some of the contaminants on the filter;

c) monitoring the reaction.

The reaction can be promoted in a number of ways, and may or may not require an initiation step. In each case however, the filter, collected sample and reaction are contained by the housing at all times, which improves the accuracy and sensitivity of the method and makes it suitable for operation by unskilled users.

Preferably, before step (a), the filter is moved from a safe position in the housing, at which the fluid cannot contact the filter, to the sampling position. Conveniently, after step (a) and before step (b), the filter is also moved to the safe position. If the particular chemistries employed require actuation, preferably the method further comprises the step of initiating the reaction. Conveniently this would occur once the filter is at the analysis position, but if appropriate it could occur with the filter at some other location. The reaction may conveniently be initiated by the introduction of a reagent to the analysis region. In this case, the reagent could be introduced once the filter is at the analysis position, in which case step (b) could comprise the steps of:

b1) moving the filter to the analysis position;
b2) sealing the analysis region so as to isolate it from the rest of the housing; and
b3) introducing a reagent to the analysis region.

Alternatively, the reagents could be introduced whilst the filter is adjacent to the analysis position and the analysis region is not fully sealed. Thus step (b) could comprise the steps of b1) moving the filter to a location adjacent to the analysis position,
b2) introducing the reagent to the analysis region
b3) moving the filter into the analysis position, and
b4) sealing the analysis region.

This would enable trapped air to escape from the analysis region.

Preferably, the method is carried out using the apparatus provided by any of the first to sixth aspects of the present invention.

Examples of sampling and analysis devices, systems and methods in accordance with the present invention will now be described with reference to the accompanying drawings, in which:

FIGS. 5a, 5b, 5c and 5d are perspective views of a device as shown in FIGS. 2a to 3b and a holster, depicting coupling of the device to the holster;

FIGS. 6a, 6b and 6c show the interior of the device during and after coupling with a holster;

FIG. 7a shows a front exterior view of the device mounted in the holster;

FIG. 7b shows a cross-section through line B-B of FIG. 7a;

FIG. 8a shows an interior front view of the device during coupling with a holster;

FIG. 8b shows a cross-section through line K-K of FIG. 8a;

FIG. 10b shows a cross-section along line C-C of FIG. 10a;

Figure 1A:
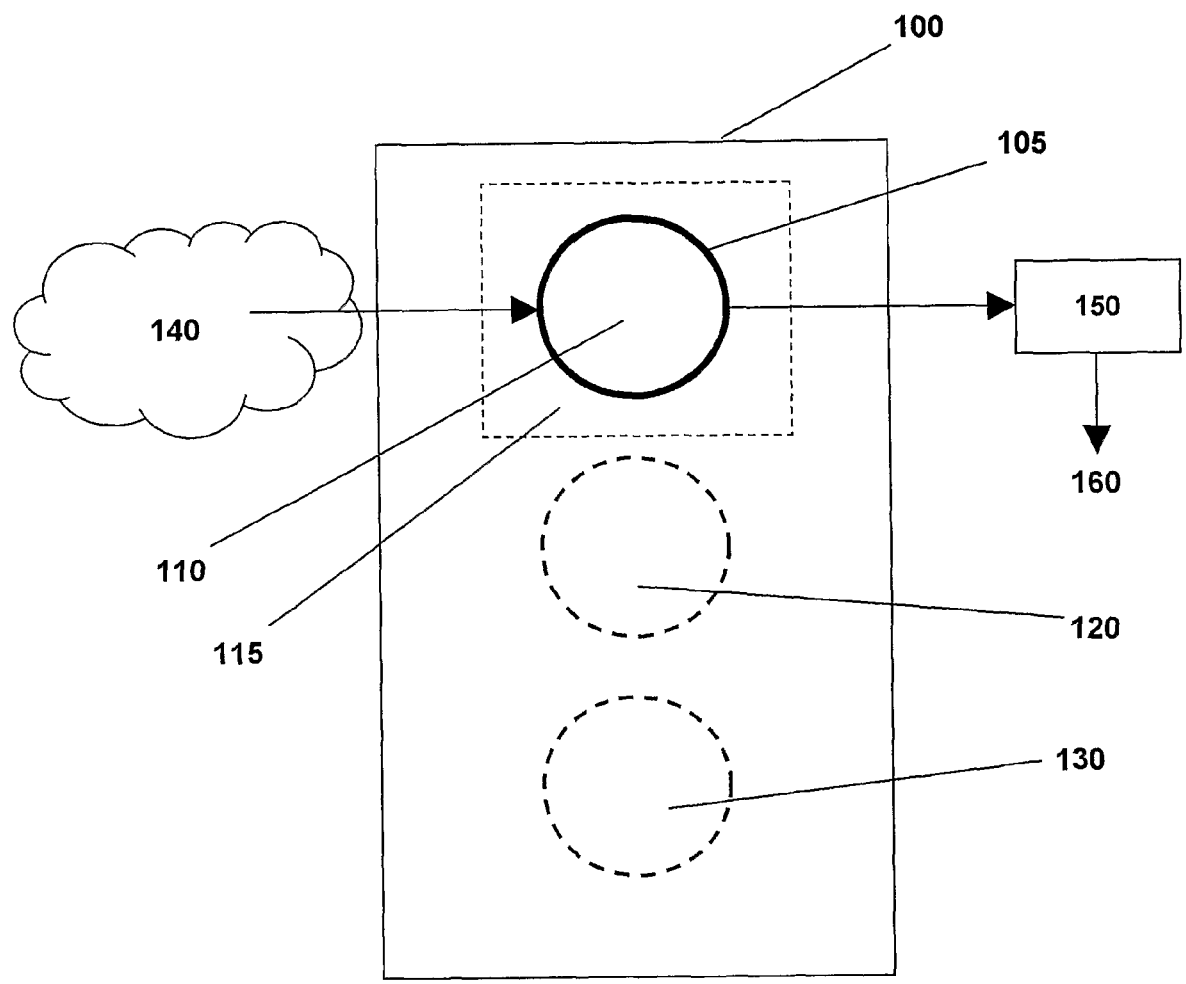
FIG 1a is a schematic representation of a sampling and analysis device with the filter in a sampling position.
Figure 1B:
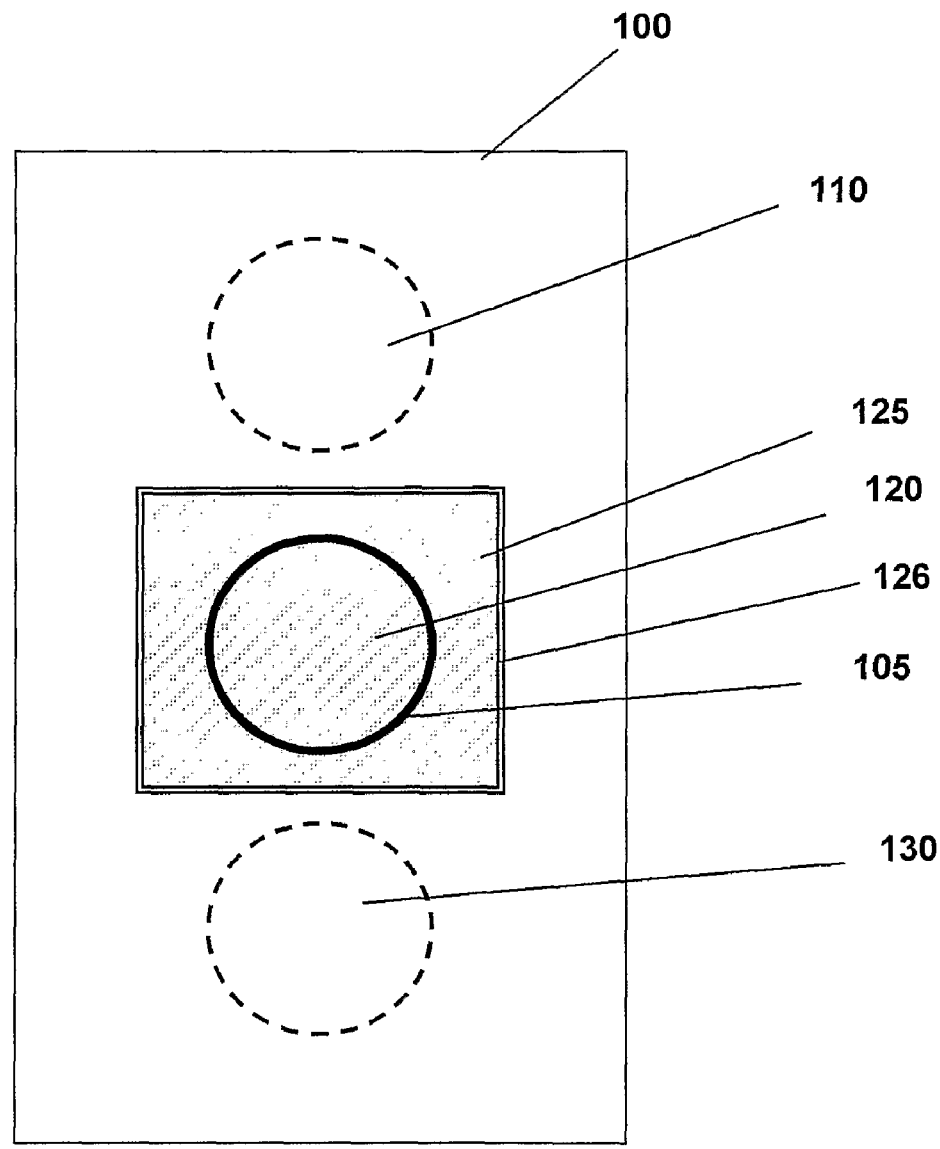
FIG. 1b is a schematic representation of a device with the filter in a safe position.
Figure 1C:
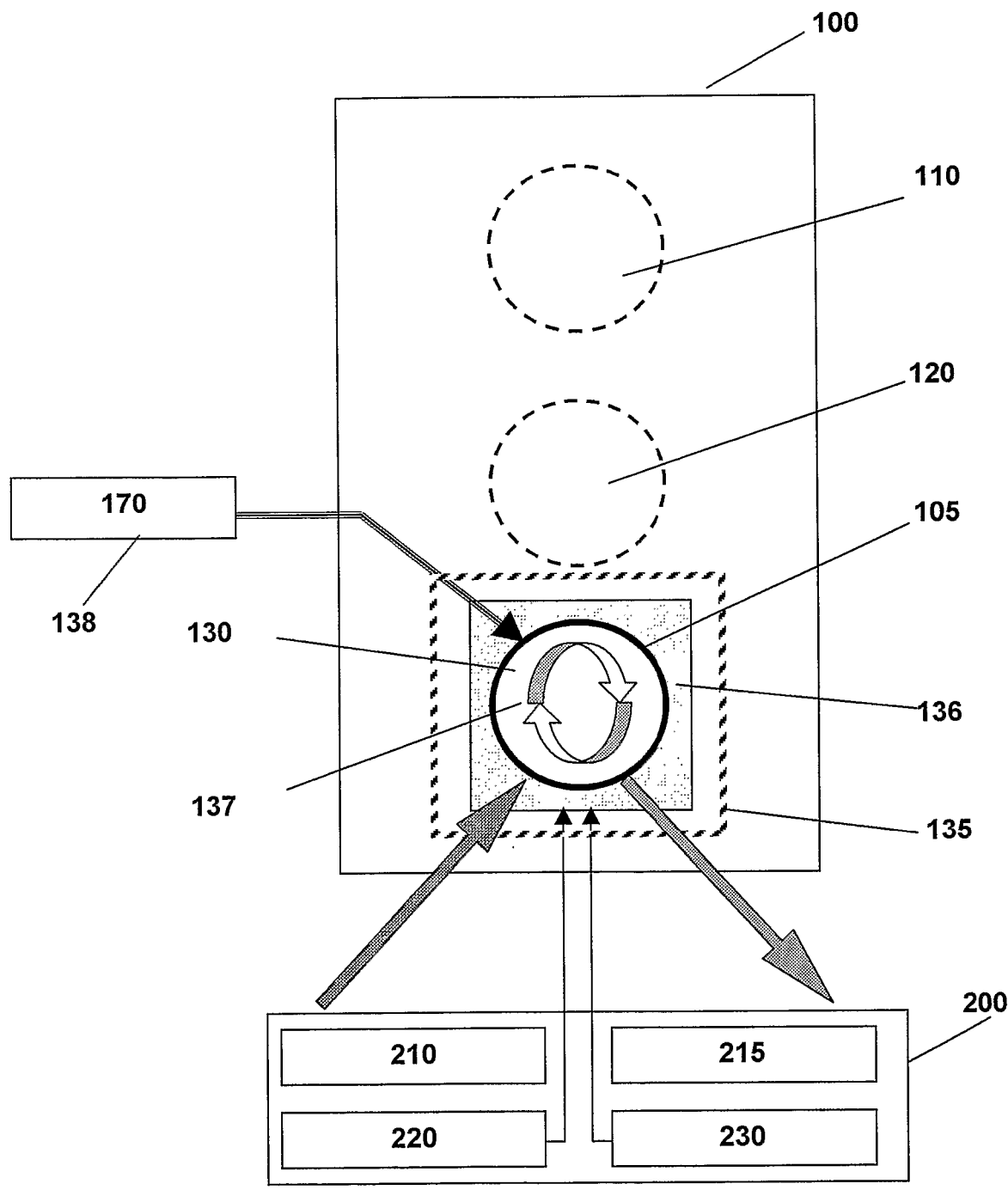
FIG. 1c is a schematic representation of a device with the filter in an analysis position, and an analyser unit for analysing a sample on the filter.

FIGS. 1a, 1b and 1c schematically depict a sampling and analysis device for monitoring of contaminants in an environment. The device is particularly suited for detection of (generally solid) airborne particles such as dust, mould spores, or enzymes as previously described. For the purposes of clarity, the following description will concentrate on the example of monitoring enzymes such as those encountered during the manufacture of washing powder. However it should be noted that the invention is not limited to this embodiment and may readily be adapted to carry out monitoring of other contaminants, whether particulate, liquid or gaseous, by selection of suitable reactions and subsequent analysis techniques. In one embodiment, for example, liquid aerosol particles carried in air may be collected. Whilst the description will focus on contaminants carried by an airstream, it is also envisaged that the device could be used to obtain samples from other fluids, including other gases as well as liquids.

Further, in this example the reaction to be monitored is activated by the introduction of a reagent, and means are provided for storing and dispensing the reagent. However, in other examples the reaction may be initiated by other techniques, such as heating or irradiating with UV light. In such cases, means for heating or otherwise activating the reaction could be provided in place of the reagent reservoir and associated parts (to be described below). Such means could be integrated into the device itself or provided externally. In still further examples, no initiation step may be required—for example, the sample could begin to react spontaneously upon collection or at some predetermined time later.

The example described is particularly suited for personal monitoring and thus adapted to be carried by a user in order to sample air from his inhalation zone. However, the same device could be used with few modifications to perform static monitoring for example by mounting the device or holster on a stand or wall.

Essentially, the device comprises a housing 100 in which a filter 105 or other collecting element is disposed. A number of regions and filter positions are defined within the housing 100. The sampling region 115 is provided with one or more apertures in the housing 100 which allow ingress of a fluid 140 to be monitored (together with any contaminants carried by the fluid) to the housing 100. Typically a second (outlet) aperture is provided for the fluid to exit the housing 100, although it could be arranged that the fluid enters and leaves via the same aperture. The sampling position 110 describes the position of filter 105 inside the sampling region 115 when the fluid is being sampled. Typically the sampling position is located between the inlet and outlet apertures so that the fluid 140 is caused to flow through the filter 105 when the filter is at the sampling position 110. A pump 150 may be provided so as to draw the fluid through the filter 105. During sampling, contaminants carried by the fluid 140 adsorb onto the filter 105, and the rest of the fluid exits via exhaust 160.

The filter is then moved, within the housing 100, to a second position. This could be an analysis position (FIG. 1c) or, optionally, a safe position (FIG. 1b). The safe region 125 provides a safe position 120 at which the filter 105 is isolated from the ambient atmosphere by means of a seal (illustrated by box 126, though in practice the seal may be positioned around the periphery of filter 105). The safe position 120 may be used to store the filter whilst the device is not in use, either before sampling or after. Since the filter 105 is isolated from the environment, contamination is prevented. The safe position 120 also ensures that any collected contaminant remains sealed and protected from premature reaction. However, after sampling, the filter 105 could be moved directly to analysis position 130 in analysis region 135. In the absence of safe region 125, removable covers could be provided over the inlet and outlet apertures so as to protect the filter from the environment when not in use.

Once the filter is at the analysis position 130 (FIG. 1c), analysis region 135 is sealed from the remainder of housing 100. Means 138 are provided for introducing reagent 170 into the analysis region 135. A dried substrate 136 may also be present in analysis region 135. Release of reagents 170 into analysis region 135 initiates a reaction with the contaminant sample on filter 105. Optionally, a stirrer 137 may be provided so as to detach the contaminant sample from the filter and to assist in mixing of the reagents.

The reaction is monitored by an analyser 200. Typically, this may be achieved by optical interrogation. For example, the analyser 200 may include an optical source 210 and an optical detector 215. Spectrophotometric techniques may be used to monitor a change in colour, for example, of the contents of the analysis region 135 through a window (not shown) in the housing 100. The analyser 200 may also be provided with a stirrer drive 220 or actuator for operating the stirrer remotely (e.g. by magnetic coupling), and a heater 230 for incubating the reaction.

Since all the sampling and analysis steps take place within one enclosure (housing 100), the device provides a convenient way of carrying out personal monitoring without the need for intervention by skilled personnel. In particular, there is no requirement to handle the filter between sampling and analysis, and the filter remains in the reaction chamber (analysis region 135) during analysis. This not only simplifies the procedure but greatly improves the device sensitivity since all of the collected sample is used in the reaction.

A particular embodiment will now be described with reference to FIGS. 2 to 12. The device or "cassette" 300 comprises a housing 1 which contains the filter 11 on which the contaminant sample will be collected, together with all of the reagents required to undertake the analysis. (In alternative embodiments, one or more of the reagents could be stored separately and added at a later stage). The device has two main parts; a housing 1 which includes, or to which are attached, features which perform functions required in the various stages of the sampling and analysis process and which retains, but allows controlled movement of, the filter 11; and, in this example, a movable filter support or "shuttle" 4 which physically supports and retains the filter. The filter support 4 slidably engages with the housing interior by means of a small clearance provided between the support 4 and the housing 1. If the filter is sufficiently robust, however, the device could be arranged without a filter support component or the supporting means could be integral to the filter.

Figures 2A, 2B:
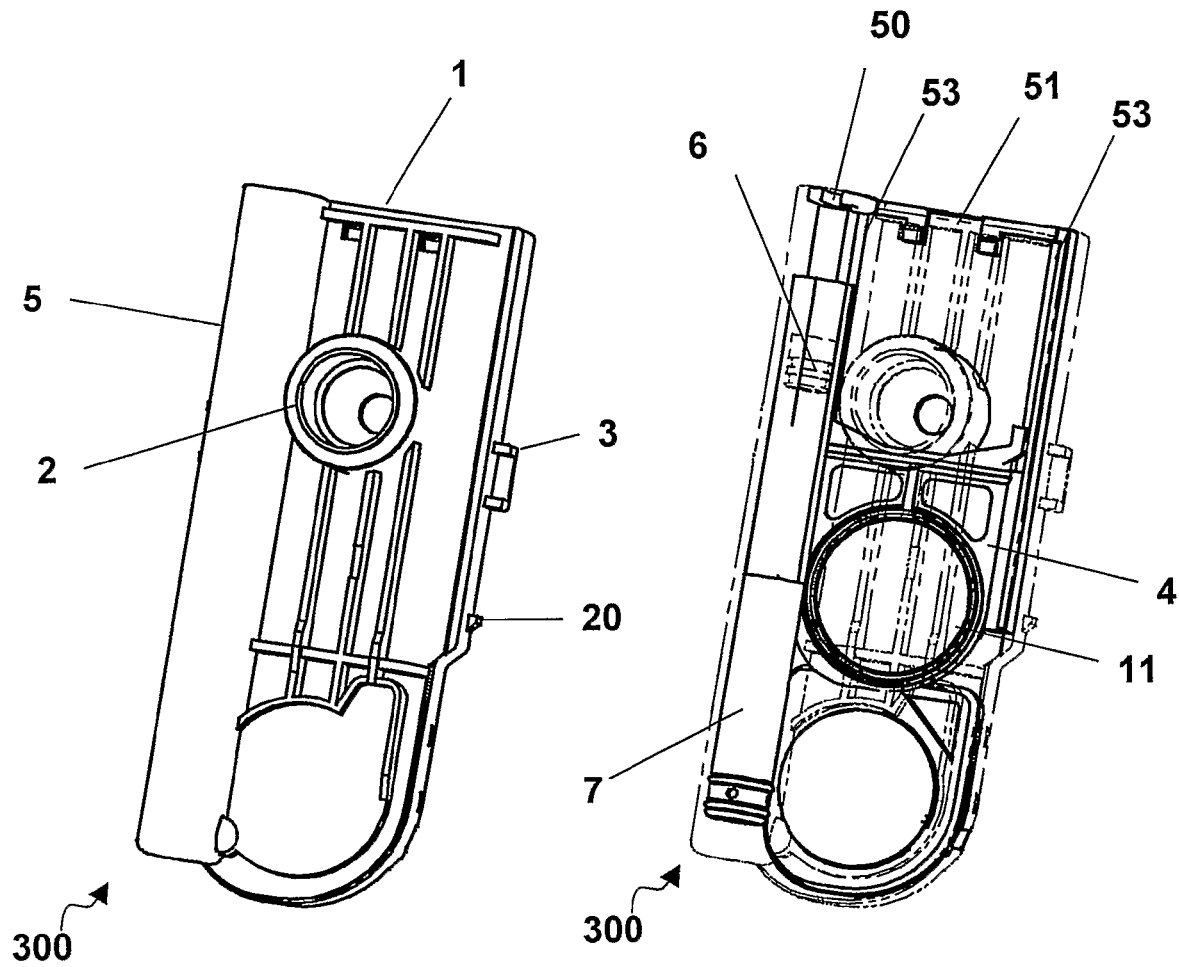
FIG. 2a is an exterior perspective view of a sampling and analysis device according to an embodiment of the present invention.
FIG. 2b is a perspective view of the interior of the embodiment shown in FIG. 2a, with the filter in a safe position.

The housing 1 is provided with an aperture 2 to allow air ingress (or other fluid entry), an aperture 2' for fluid egress (FIG. 4A) and a reservoir region 5 in which reagents are stored prior to use. FIG. 2B shows the interior of the device 300 as supplied. The filter support 4 holds the filter 11 in an area sealed from contact with the ambient environment, designated the safe region. The filter 11 is said to be in the safe position. This prevents contamination of the filter prior to the intended sampling period, and, after sampling, also stops the collected sample from dispersing throughout the rest of the housing 1, for example during transport. In particular, the sample is not able to access the analysis region thereby preventing premature reaction. In this form, the device 300 may be stored for an extended period, limited only by the shelf life of the reagents stored therewithin to be employed in the analysis phase.

FIG. 2B also shows the interior of reservoir region 5 having a reagent reservoir 7 and piston 6. In this embodiment, the reservoir 7 is a barrel. This will be described in greater detail below.

Apertures 50, 51 and 53 are provided in the housing to allow the filter support 4, reservoir or barrel 7 and piston 6 to be moved or operated from outside the housing 1, as will be explained below.

The housing 1 is further provided with a holster key 3 and a locking pin 20 which enable the device 300 to interlock with a holster.

Figure 3A:
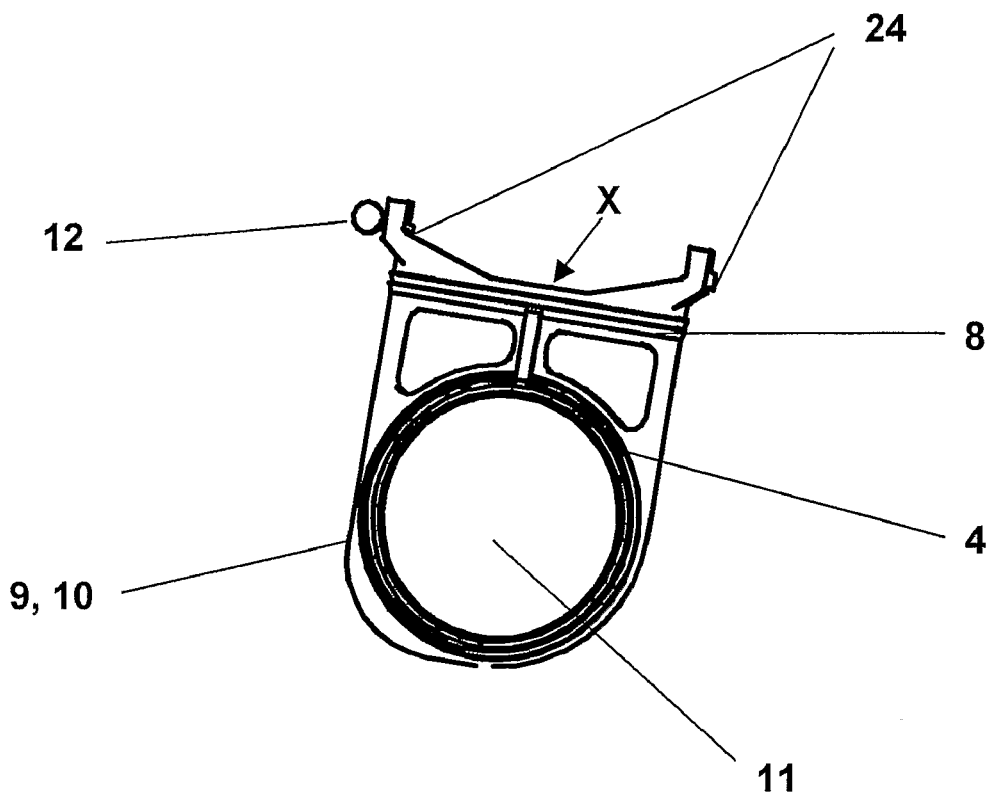
FIGS. 3a and 3b are perspective views of a filter support used in the embodiment.
Figure 3B:
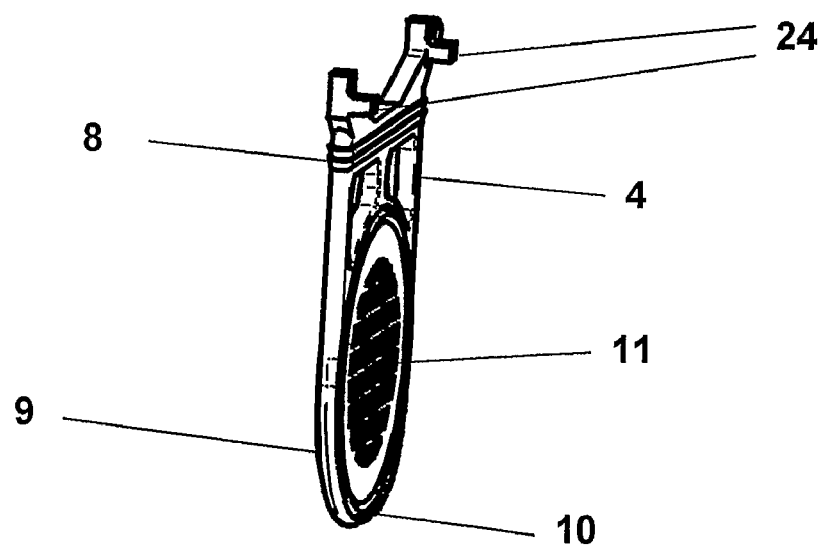

FIGS. 3a and 3b show two views of the filter support 4 and filter 11 located thereon. Filter 11 may be retained on the filter support 4 by a variety of means, but heat staking is convenient and effective. The filter support or shuttle 4 is provided with a shuttle seal 8 which extends around the filter support 4. The seal 8 could comprise a single seal (as shown) or two separate, parallel seals. When the filter support 4 is enclosed within the housing 1 at certain positions, shuttle seal 8 provides a barrier extending between filter support 4 and the interior wall of the housing 1 which effectively isolates the regions of the housing below seal 8 from those above. Thus fluid communication is prevented across seal 8. In practice, seal 8 need not provide a complete seal when the filter is in the sampling or safe positions. Here, filter seals 9 and 10 provide the seal (see below). There may be a path around the end of seal 8 according to the shape of the housing interior in the vicinity of the sampling and safe positions. However, in the analysis position, the seal 8 fits to the housing and a complete seal is provided, closing the analysis region. The shuttle 4 may have notches (not shown) along its side struts to prevent capillary action transporting fluid (in particular, reagents after actuation) between the shuttle and the interior walls of housing 1. Alternatively, the side struts may be removed and connection between the region of seal 8 and that of the filter 11 on the shuttle provided by means of a (reinforced) centre strut instead. Similarly, seal 8 may be greased to prevent capillary action taking fluid past the seal. Indeed, all the device components could have a water-repellant coating applied.

Figures 4A, 4B:
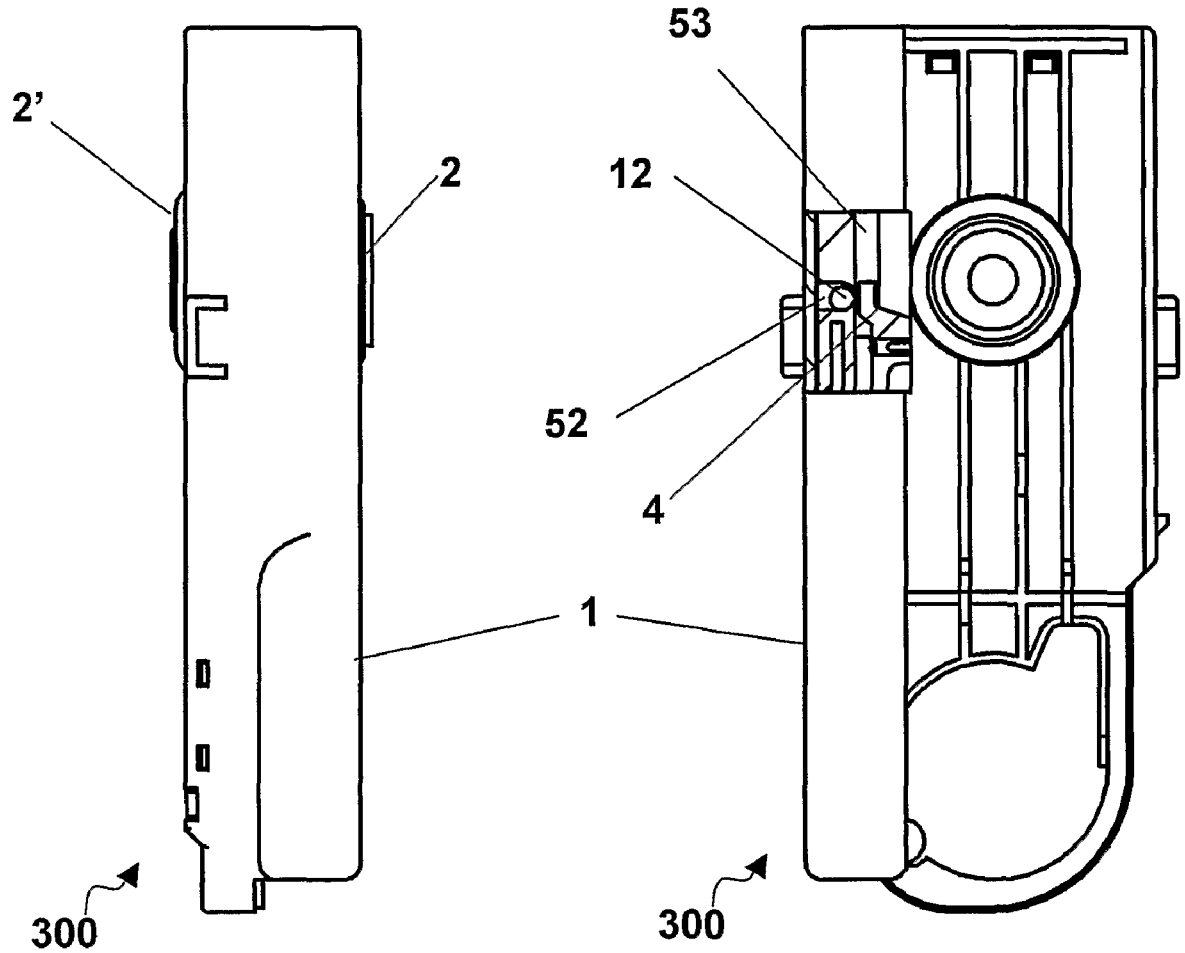
FIG. 4a is an exterior side view of the embodiment.
FIG. 4b is a exterior front view of the embodiment showing a detail of the interior arrangement.

Annular filter seals 9 and 10 are located on each side of the filter support 4 around the perimeter of the filter 11. In the safe position, the filter seals 9 and 10 extend between filter support 4 and the housing interior, effectively isolating the filter from the rest of the device. This not only helps prevent contamination from the environment but also prevents premature reaction between the sample and reagents which may be present in an analysis region (see below). Tabs 24 are provided which may be accessed through elongate apertures 53 (shown in FIGS. 2b and 10). In use, the filter support 4 can be slid relative to the housing 1 by insertion of a suitable implement through the elongate apertures 53 to engage with the tabs 24. In the present embodiment, such an implement is provided on the holster, as will be described below. The retention pip 12 is provided to lock the shuttle 4 into the safe position, before first use, as shown in FIG. 4b. The retention pip 12 mates with socket 52 inside the housing 1. This feature provides an additional level of security by ensuring that the filter support 4 is not unintentionally moved from the safe position prior to first use, thereby preventing accidental contamination of the filter 11. The retention pip 12 is designed to snap off from the filter support 4 on first use, remaining in socket 52. Thereafter, the filter support 4 may be moved inside the housing 1 as will be described below.

Once ready for use, the filter must be moved from the safe position to a sampling position in a sampling region. The sampling region is that part of the housing 1 which is provided with inlet aperture 2 and outlet aperture 2'. The sampling position is located between the inlet and outlet apertures 2 and 2'. Moving the filter 11 to the sampling position could be achieved manually or using a motor. However, in this embodiment, the device 300 is configured to couple with a holster 15. The coupling action itself moves the filter 11 into the sampling position.

During the sampling process, the device 300 remains mounted on the holster 15 (see FIG. 5) which in turn connects to a sampling pump (not shown). For example, a standard personal sampling pump such as those available from SKC and Casella may be employed.

The holster 15 is designed to couple with housing 1 of the device 300. Means are provided on the holster 15 so as to move the filter from the safe position to the sampling position inside housing 1 as the device 300 is slid into the holster 15.

FIGS. 5a and 5b show separate views of the device 300 and holster 15, illustrating insertion guides 30 on the sides of the holster 15, together with forks or protrusions 25 and an aperture 31 which facilitates gas flow through the apertures 2 and 2' in the device housing and the filter 11 when it is in the sampling position. The holster 15 is also provided with features 21 and 22 which engage with the holster key 3 and locking pin 20 on the device 300.

FIGS. 5c and 5d show the insertion process of the device 300 into the holster 15. In the first instance, the device 300 is positioned at an angle to the holster 15 with one end 60 of the housing 1 just inside the cavity formed by the holster 15. The holster key 3 is simultaneously aligned with recess 21 and the housing 1 is pressed back towards the holster so that the rear face of the housing 1 (having outlet aperture 2') is in contact with the holster face 61. A downward movement of the housing 1 as shown in FIG. 5c then completes the mating operation and locking pin 20 mates with an internal latching hook which pivots around point 22, thereby locking the device 300 into the holster 15. It may be released by depressing button 29 which retracts the hook and allows the device 300 to be slid out of the holster 15.

During the coupling procedure, forks or protrusions 25, provided on face 61 of the holster 15, lock with tabs 24 on the filter support 4 through elongate apertures 53 in the housing 1. As the housing 1 is moved downwards relative to the holster 15, the filter support 4 is fixed relative to the holster 15 by cooperation between tabs 24 and protrusions or forks 25. The housing 1 slides relative to the filter support 4 thereby bringing the filter 11 into the sampling position. Thus, once mounted in the holster 15, the filter 11 is exposed to the environment and the device is ready to obtain a sample for analysis.

Figures 6A, 6B:
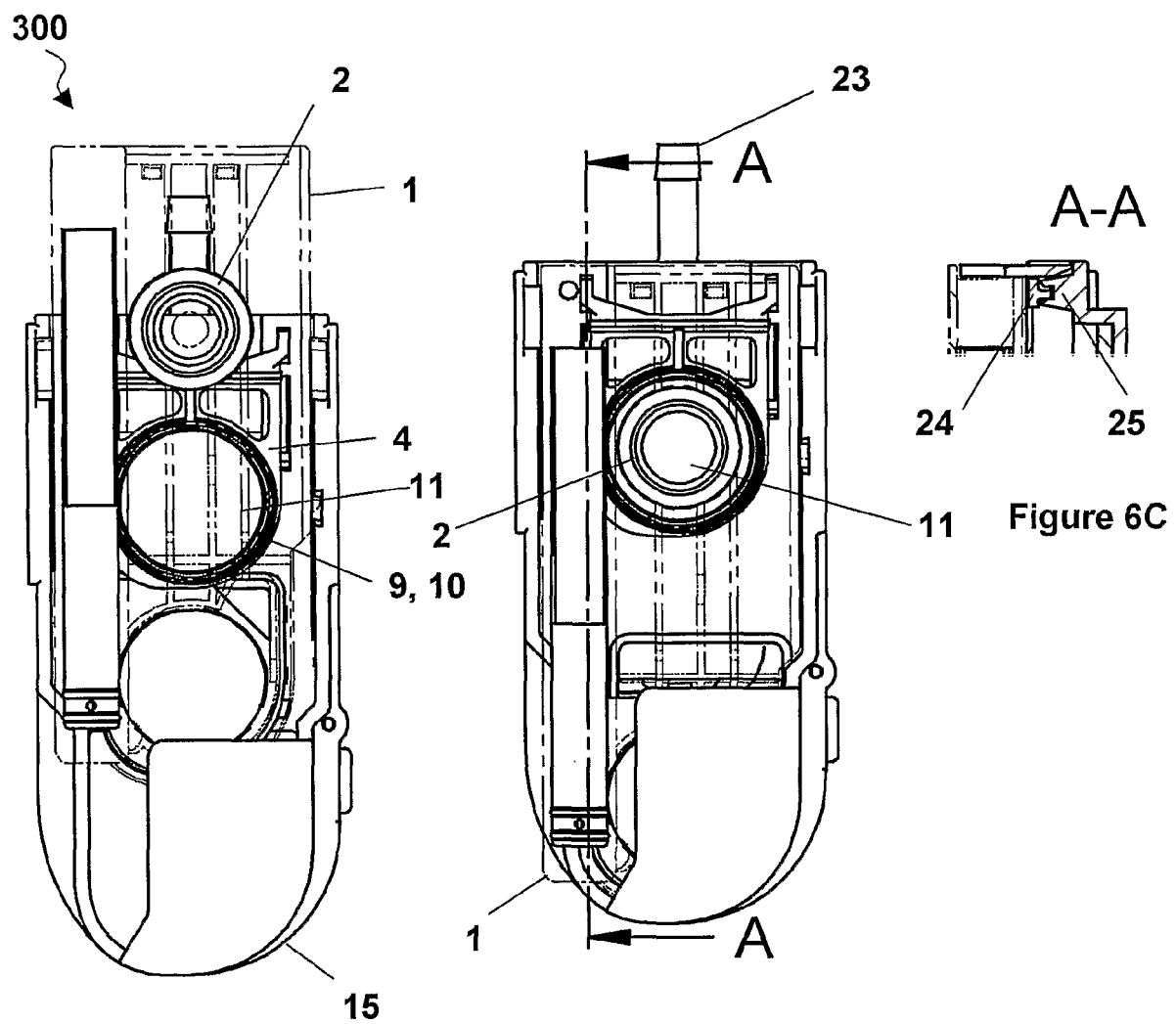

Further cross-sectional views of the device 300 being inserted in to the holster 15 are shown in FIGS. 6a, 6b and 6c. The detail in FIG. 6c illustrates how tabs 24 on the filter support 4 mate with forks 25 on the holster 15, thereby fixing the filter 11 over aperture 31. Further insertion of the device 300 causes the housing 1 and filter support 4 to slide relative to one another and so bring inlet and outlet apertures 2 and 2' into alignment with the filter 11 as shown in FIG. 6b.

Figures 7A, 7B:
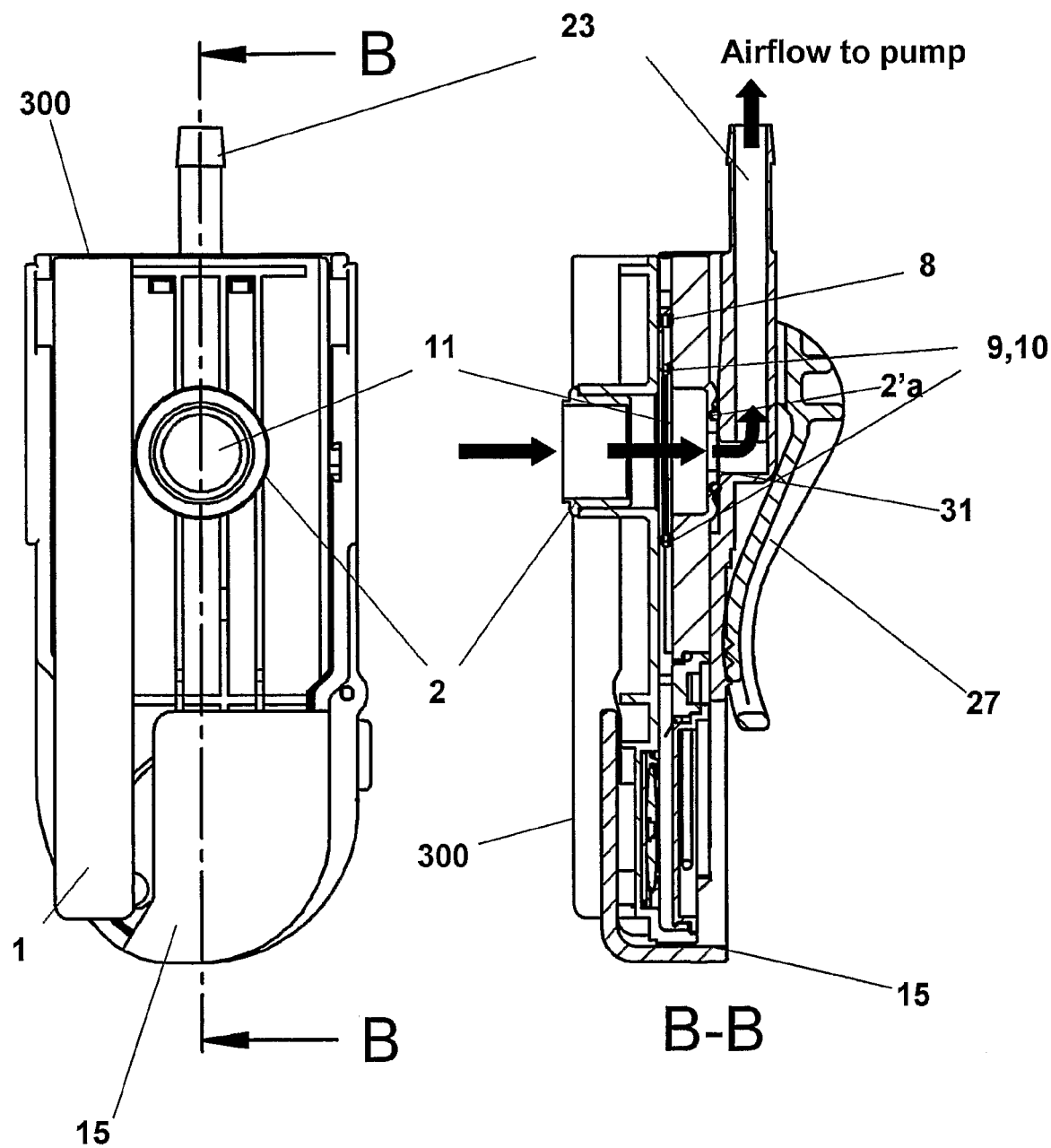

FIGS. 7a and 7b illustrate the device and holster assembly during the sampling process. A pipe 23 connects the assembly via a hose (not shown) to a sampling pump (not shown). Air is drawn (as shown by the arrows) though inlet aperture 2, filter 11, outlet aperture 2', holster aperture 31 and lastly pipe 23 by the action of the pump. An O-ring 2'a or equivalent bondable rubber moulding is disposed around outlet aperture 2' to improve the seal between the device and the holster. Pumps of the type typically employed in such sampling may be provided with microprocessors to ensure that the sampling period and flow rate is accurately recorded or controlled, since the amount of enzyme (or other contaminant) collected is dependent upon these parameters as well as the concentration of the measurand in the atmosphere. Filter seals 9 and 10 prevent any leakage of air around the filter and so ensure the integrity of the sample obtained. Air flows through the filter 11 in a controlled fashion in order to deposit a reliable and quantitative sample of the contaminant on filter 11. A clip 27 is provided so that the assembly may be worn close to the breathing zone of the user for extended periods of time without restriction of movement. Alternative attachment methods may be envisaged, depending on the user requirements and the nature of the clothing worn.

Figures 8A, 8B:
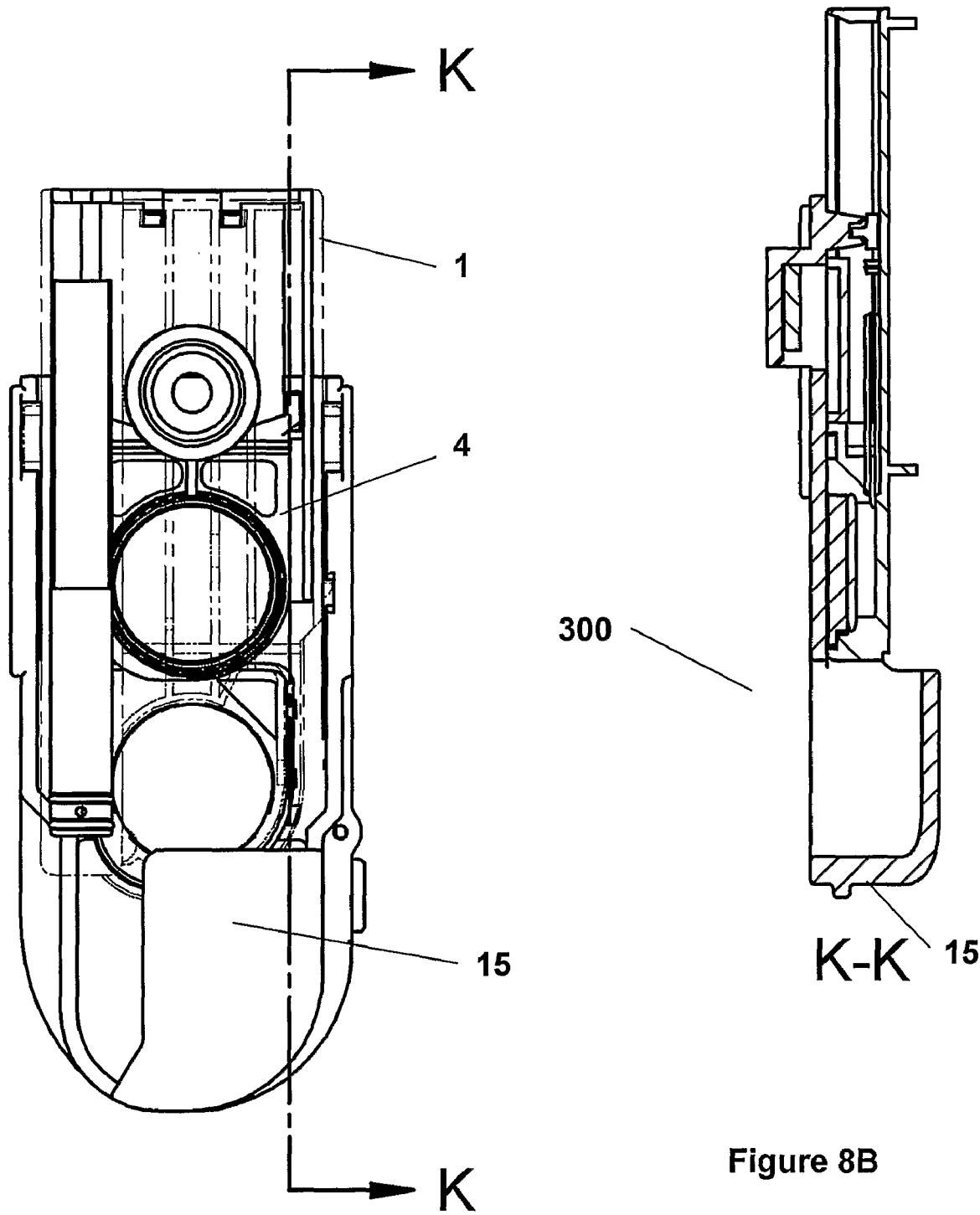

On completion of the sampling process, the device is withdrawn from the holster 15 by depressing button 29 to release the locking hook, and sliding the housing 1 back out, essentially reversing the insertion process described above. This movement returns the filter support 4 to the safe position, thereby preventing contamination of the filter and minimising the loss of any of the contaminant collected. This is shown in FIGS. 8a and 8b. In this embodiment, the arrangement is such that the device 300 could be reused for further sampling periods if desired. In principle, repeated movement of the filter 11 to and from the sampling position is possible, depending on the detailed design of the system. This might be advantageous if, for example, it were desired to undertake sampling over an extended number of working shifts and integrate the sample onto a single filter. However, in some circumstances a single use arrangement is preferred in which case the device may be provided with "non-return" features or similar which ensure that only a single exposure of the filter 11 is feasible. For example, the latching hook may be arranged so as to prevent reinsertion of the cassette following the first withdrawal from the holster 15. This approach may have advantages in certain personal safety monitoring applications.

When the user wants to analyse the collected sample, which may be immediately after sampling or at some later time, the device is fitted to an actuator or slid into a receiving mount or socket forming part of an analyser (not shown). In this example, insertion of the device into an analyser automatically instigates a sequence of events to produce the quantitative measurements required. For example, proper insertion of the device into the analyser or closing of a lid on the analyser could indicate to the analyser that the cartridge is ready for analysis. Subsequently, the analyser may "activate" the cartridge by moving the filter into the analysis position and releasing the reagents. These actuations could occur simultaneously or in sequence. The reaction is then monitored as will be described below. Of course it would also be possible to operate the analyser manually. The precise order in which the process steps occur depends upon the details of the chemistry and interrogation methods employed.

Alternatively, separate analyser and actuator components may be used. In this case, the analyser is not provided with means for moving the filter or actuating release of reagents, although it may retain other elements of control, for example stirring or heating. A separate mechanism is provided to "actuate" the cartridge. Such an actuator (not shown) couples with the housing and includes a number of rods which extend into the device to drive movement of the shuttle 4, the barrel 7 and the piston 6 (described below). The actuator may be manually or electrically driven and may be fully or partially automated, potentially controlled by a single switching action. It is envisaged that the device be activated by use of the actuator and then placed (either with or without the actuator) in the analyser for measurement. The actuator could be hand-held, clipped to the device housing, fitted to the analyser during actuation, permanently attached to the analyser, or both the actuator and the analyser could be attached to some other frame component.

Whichever actuation apparatus is used, at the onset of the analysis procedure, the filter is moved from the sampling or safe position towards the analysis region. The mechanics of this procedure will be described in more detail below. The filter may either be directly moved to the analysis position or could be retained at a location adjacent to the analysis position while the reagents are introduced to the housing. This latter technique allows trapped air to escape before seal 8 fully isolates the analysis region. Once the reagents are introduced, the movement of the filter to the analysis position would be completed as described below.

In this example, the analyser is provided with means for moving the filter 11 to an analysis position. This could be achieved, for example, by providing the analyser with protrusions similar to forks 25 on holster 15 which couple with tabs 24 on filter support 4. Alternatively the protrusions on the analyser could be themselves movable and used to mate with the filter support 4 and then move it into the analysis region at some predetermined time after insertion of the housing 1 into the analyser. In the preferred example, however, other means for moving the filter into the analysis position are envisaged. The analyser is provided with an analysis actuator component which is inserted through aperture 51 in the housing 1 to push filter support 4 towards the analysis position. If a separate actuator component were used, the analysis actuator component, or equivalent, would be provided on the actuator rather than the analyser. Typically the component would be in the form of a rod or shaft and would contact the top portion of the filter support 4 (for example at the position "X" shown in FIG. 3a). This action moves the shuttle 4 such that the shuttle seal 8 mates with the internal surface of the housing 1 in order to provide a liquid-tight seal, thereby fully enclosing an analysis region or chamber and isolating it from the rest of the housing 1.

Figures 9A, 9B, 9C:
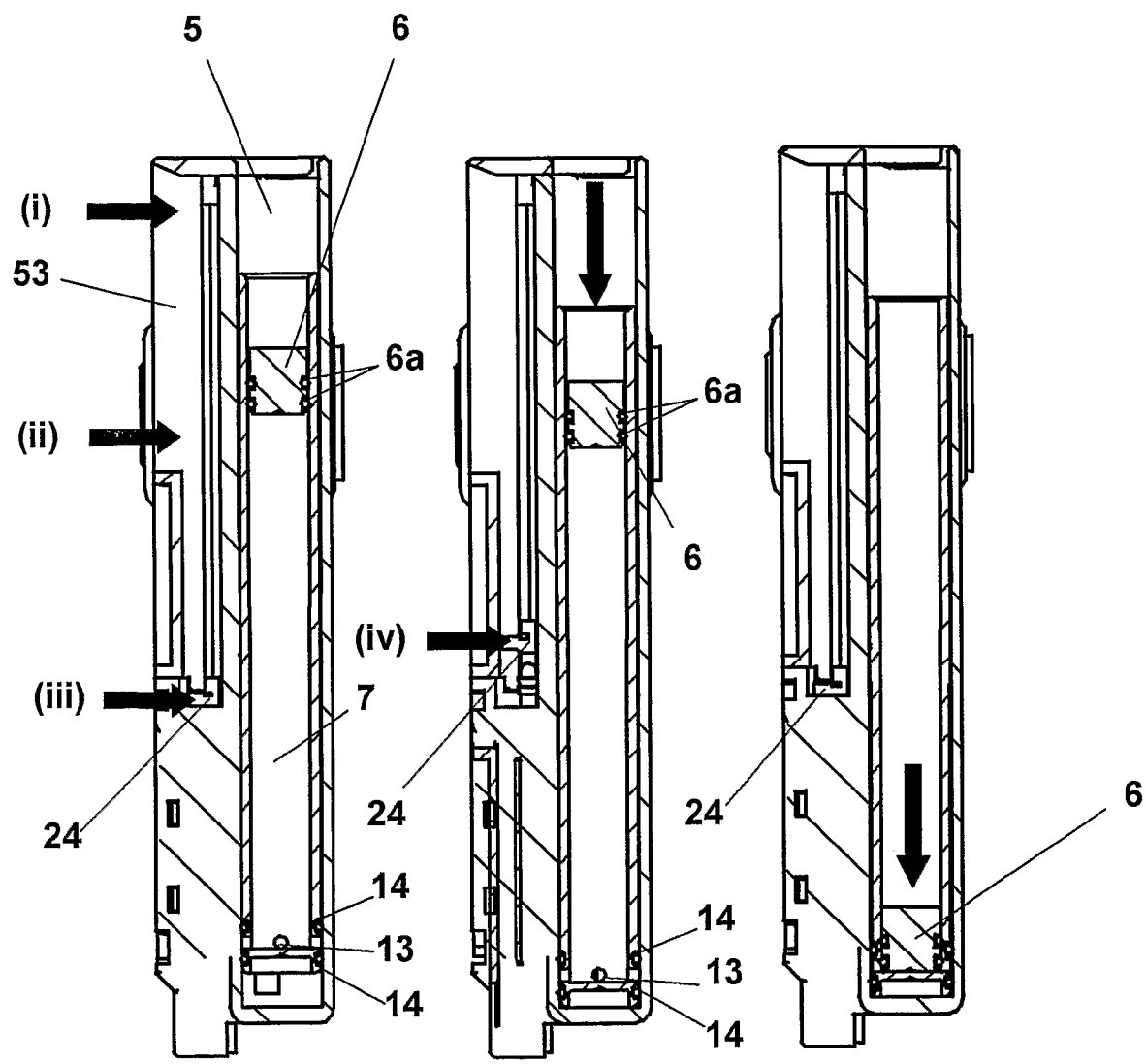
FIGS. 9a, 9b and 9c show an interior side view of the device before, during and after introduction of a reagent into an analysis region of the device.

Arrows (i) to (iv) on FIGS. 9A and 9B indicate the approximate positions of the tabs 24 on the filter shuttle 4 at various stages of the sampling and analysis procedure. In the safe position, the filter shuttle rests with tabs 24 at position (ii). The shuttle is moved up so that the tabs are adjacent to (i), where the filter is in the sampling position. At the start of the analysis sequence, the shuttle may be moved either directly to the analysis position, with tabs 24 at position (iii), or to position (iv), adjacent to the analysis region. In the latter case, reagents will be introduced to the analysis chamber and then the shuttle will continue to the analysis position.

Reagents are introduced to the analysis region from reservoir region 5. This avoids potential errors and effort involved in making and pipetting reagent solutions into the analysis region. The analyser (or actuator) may be provided with a mechanical actuator which acts on the reservoir or barrel 7 and piston 6 via aperture 50 to release a predetermined dose of reagents held in the reservoir or barrel 7 as shown in FIGS. 9a, 9b and 9c. The piston 6 is typically a one-piece moulding made of rubber material which incorporates O-rings 6a. At least one passage 13 is provided at the end of barrel 7 which allows the reagents to escape from barrel 7 into reservoir region 5 from which there is an exit into the analysis region. O-rings 14 are provided either side of passage 13 so as to confine escaped reagent within a small volume of reservoir region 5, away from the exit leading to the analysis region. Alternatively, the O-rings 14 may be replaced by bondable rubber mouldings. Actuating rods (not shown) act on the barrel 7 and piston 6. The barrel 7 is moved so as to align the passage 13 with the exit from reservoir region 5 to the analysis region (FIG. 9b). The piston 6 then moves to dispense liquid through the aligned ports and the dose of reagent is released. Typically movement of the barrel 7 is effected by a separate actuating component from that acting on the piston 6. Two separately moveable parts (not shown) enter through the aperture 50, one to interact with the reservoir or barrel 7 and the other with the piston 6. Although this example utilises a barrel and piston arrangement for storing and dispensing of reagents, other approaches are also envisaged. For example, the reagents could be contained in a reservoir adjacent to the analysis region in the housing 1 with a seal which is broken by the filter support 4 as it moves into the analysis position. The reagents are released and fill the analysis regions surrounding the filter 11, washing the enzyme sample off and initiating the required enzyme catalysed reaction. Alternatively, the analysis region could be provided with an inlet or valve through which reagents could be manually injected. For ease of assembly, a portion of the wall of the analysis region may be in the form of a cover which is attached to the rest of the housing during manufacture. This must be sealed to the rest of the body to prevent escape of reagents, and this may be achieved by an O-ring or, preferably, a bondable moulded material attached to the cover.

Further, in this example, the whole dose of reagent is dispensed in one step. However, for some applications a multi-stage reagent release may be appropriate. Here, the reagent is released in several controlled amounts, for example by a series of piston movements. This could be employed to provide several washing steps, for example.

A liquid reagent containing buffer and detergent is normally employed, but other approaches are also feasible (e.g. using gels). Preferably, reagents are selected which will not interact with the cartridge materials, and in particular will not affect the mechanical properties of the housing, shuttle, seals or other components.

Figure 10A:
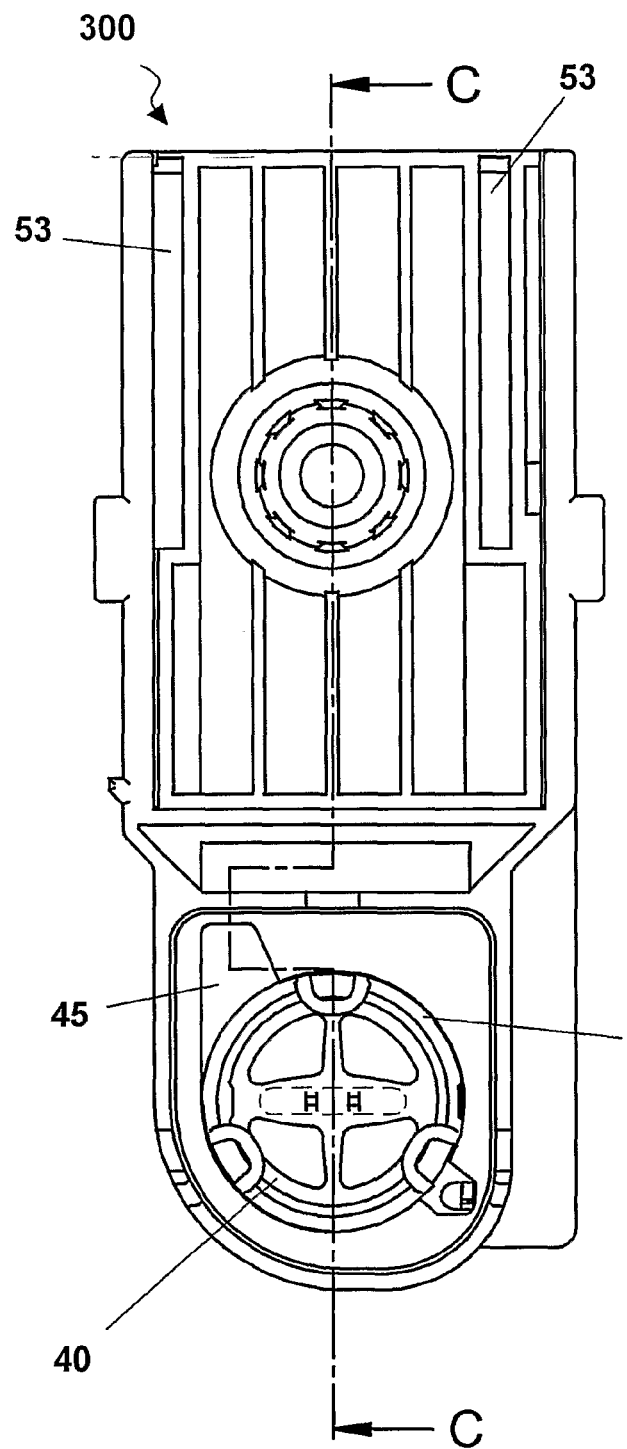
FIG. 10a shows a front view of the device with the filter in the analysis position and a stirrer positioned adjacent to the filter.
Figure 10B:
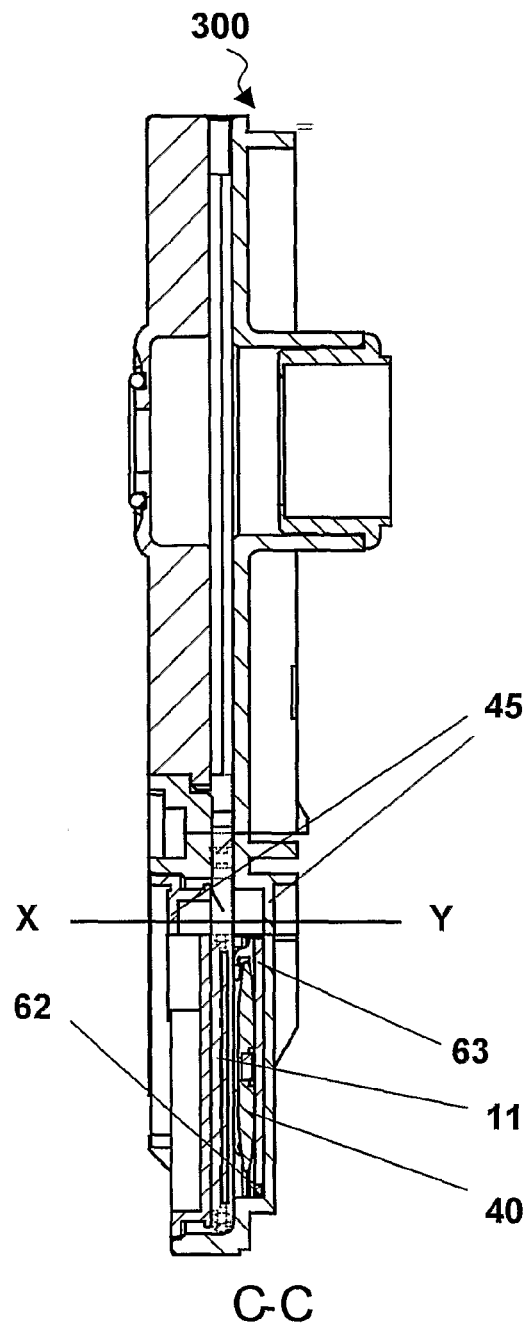
Figure 11:
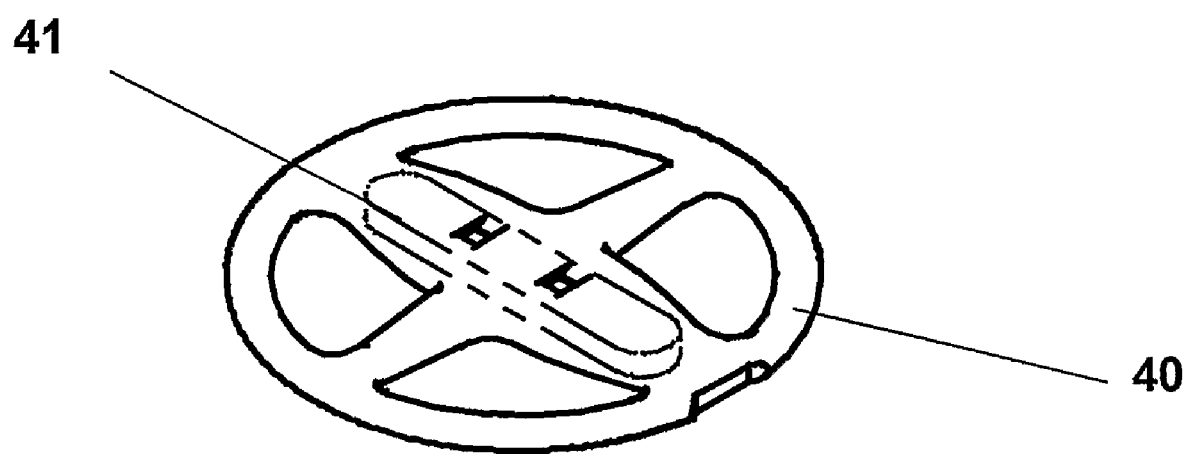
FIG. 11 shows an example of a stirrer which may be incorporated into the device.

Typically, a "substrate" is also provided in dry form on an absorbent pad 63 (FIG. 10b). The substrate is the starting chemical for the reaction and is generally not stable in solution. The pad 63 is typically a glass fibre material of the type supplied by Millipore (e.g. GFCP203000). When liquid or gel reagents are released into the analysis region, the substrate is dissolved and the reaction initiated. As such, even if a dry "substrate" is employed, the analysis generally takes place in the liquid phase.

To assist the reaction, a stirrer may be provided to mix the reagents. The analysis region contains a magnetic stirring element 40 as shown in FIGS. 10a and 10b, and in greater detail in FIG. 11. This is provided with a magnetic or steel cross member 41, thereby facilitating magnetic drive from a motor outside the housing 1. This arrangement allows stirring during analysis without introducing a further body into the device and thereby minimises the risk of contamination. Conveniently, the motor or other stirrer actuator is integrated within the analyser. Alternatively, with appropriate design modifications to the housing, a mechanical drive linkage for the stirrer 40 may be provided. Stirring may be continuous or, preferably, intermittent.

Movement of the filter support 4 into the analysis region brings the enzyme-loaded filter 11 into close proximity with the substrate pad 63, with the stirrer 40 between the two. The magnetic drive is preferably positioned so that stirrer 40 is attracted to rotate on the surface of pad 63, but does not contact the filter 11, thereby preventing filter breakup. The filter 11 may also be held away from the stirrer 40 by a protective cage 62 and/or the attachment of the filter 11 to the filter support 4. Cage 62 also ensures that the stirrer 40 is retained and rotates in the correct position relative to the remaining components in the cassette.

Figure 12:
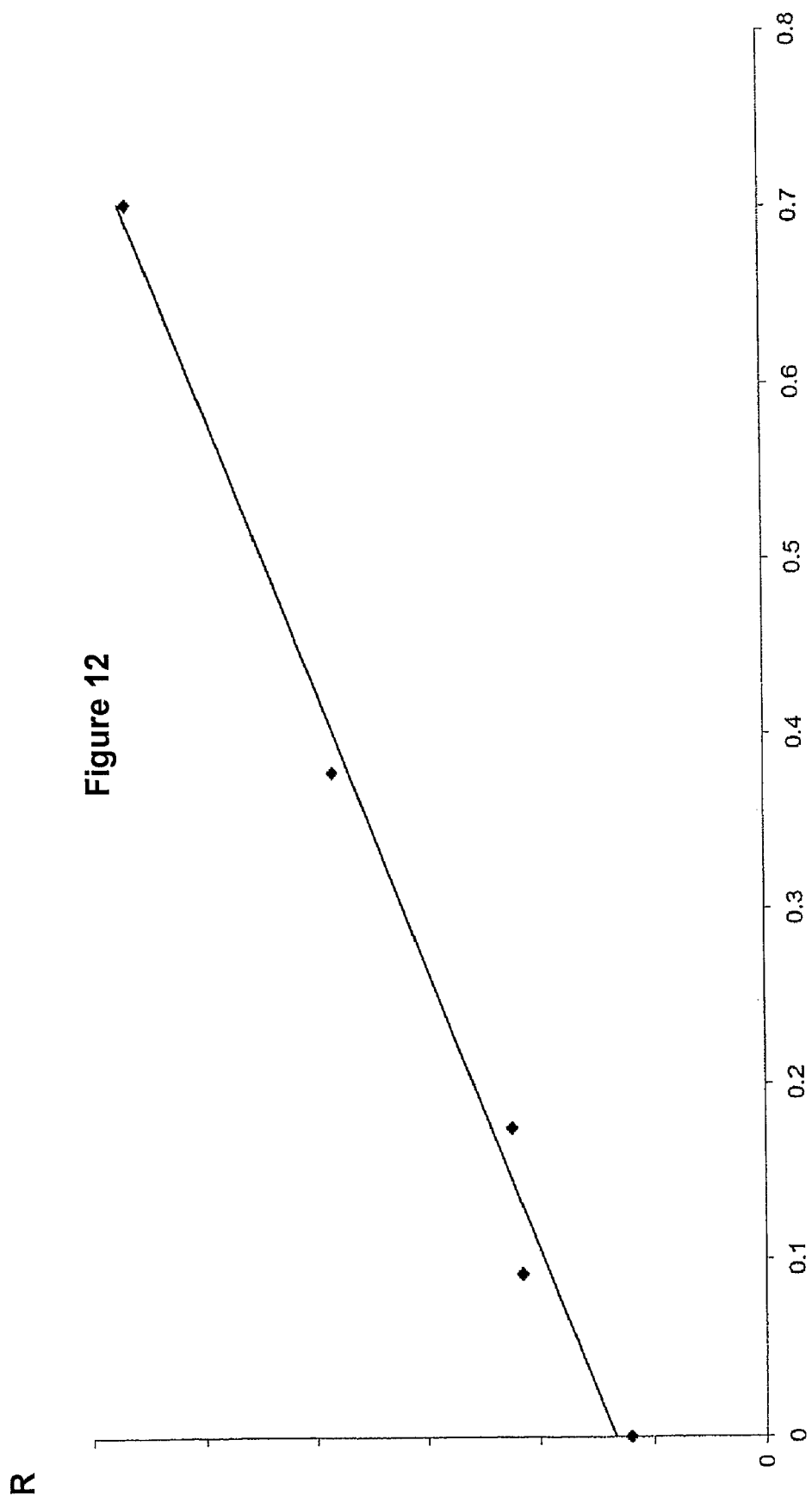
FIG. 12 is a graph showing results obtained using the embodiment depicted in FIGS. 2 to 11 to detect Savinase.

It is a particular advantage of this arrangement that the filter and sample material remain in the analysis region, instead of using a solution of extracted enzyme as in conventional methods. There is no loss of enzyme, and any remaining on the filter still contributes to the generated signal. Ability to stir and interrogate (see below) the reacting mixture in situ removes the need for the filtering step employed in conventional analysis methods, since breakup of the filter is minimised. Any enzyme retained by the filter is not lost and can still contribute to the reaction. Even if the extraction stage (detachment of the sample from the filter 11) is marginally less effective than in methods where the filter virtually disintegrates, the overall detection process is more efficient due to the complete retention of collected enzyme in the analysis region. For example, the detection limit for Savinase (a typical detergent protease) using the system is below 0.5 ng per ml which is significantly better than the values generally achieved by conventional methods (see above). The device thus achieves high sensitivity and low detection and quantification limits. FIG. 12 illustrates the consistent results achieved using apparatus and methods as described to detect Savinase. The rate of increase of colour density, R, is plotted against the protein concentration, P, in ng/ml.

During a defined part of the analysis process, the analysis region may also be heated by direct or indirect means provided by the device or by the analyser. Typically, the reaction is promoted by incubation at a temperature of approximately 40-50° C.

The analysis region is provided with means for monitoring the contents of the region. Typically, progress of the reaction is detected by means of optical interrogation though windows 45 (FIG. 10). For example, transmissive spectrophotometric techniques may be employed to detect changes in the colour of the reaction mixture, as will be described in greater detail below. Alternatively, the analysis region could be provided with electrodes and the monitoring carried out using electrochemical methods such as amperometry or voltammetry.

The particular reagents selected, and the reaction required, will depend on the particular enzyme or other contaminant under observation. In this example, the reaction is similar to that described above with respect to known methods of analysing domestic allergens. It should be noted however that these chemistries are not the "industry standard" approach for detection of subtilisin in industrial environments. The reaction generates a yellow colour which may be readily detected in a spectrophotometer by absorbance at a known wavelength, in this case approximately 395 nm. It is advantageous to measure the rate of the reaction so as to limit the effect of interference. As well as the enzyme, the collected sample will contain general industrial dust, and a single absorbance measurement may not allow their relative contributions to the signal to be determined: "background dirt" could be the major proportion of the signal. By measuring the rate of increase in absorbance as a function of time, a measure of the contribution due to the enzyme reaction alone is obtained. Other contaminants simply increase the background against which such measurements are made. Since absorbances from different sources are additive, a higher baseline is not generally a problem.

For very sensitive detection, such rate measurements alone may be inadequate. As the background dirt precipitates out in the mixture, the (high) background signal may not remain constant. By employing measurements at additional wavelengths where there is no contribution from the enzyme-driven reaction, it is possible to determine the rate of the changes in background signal and hence compensate the reading at the measurement wavelength (e.g. at 395 nm). For example, absorbances at wavelengths of approximately 525 nm, 595 nm and 630 nm may additionally be observed.

Alternative interrogation techniques could be used in place of spectrophotometry. For example, fluorescence has been shown to work using commercially available substrates labelled with fluorescent dyes (Amido methylcoumarin compounds) instead of yellow colours. Electrochemical methods are also quite appropriate and could benefit from aspects of the housing design. For example, 4-aminophenol (4AP) derivatives could be employed in amperometric or voltammetric systems.

During and on completion of the analysis step, the seals 8, 9 and 10 (in particular seal 8) within the device ensure that waste reagents and products are retained within the housing 1. This is a particularly important consideration when employing hazardous materials. Correct disposal techniques may be applied without risk of contamination to the user.

The device 300 may be provided with a bar code or other identification features so that the sample data can be readily added to individual exposure records. For example, on insertion of the device 300 into the analyser, results may be automatically downloaded to a database, allowing at-risk individuals or hotspot areas within the sample zone to be identified.

The detergent industry uses a range of closely related subtilisin enzyme types, all of which may be detected using essentially the same chemistry (although the optimum reaction conditions for each might be slightly different). Therefore, the responsivity and calibration of the system towards varying concentrations of these different forms is an important issue. In practice, it is very difficult to produce a "standard" loaded dust atmosphere containing a known amount of the target enzyme, and so a full test of the sampling and analysis system under the intended operating conditions is difficult to achieve.

In conventional systems using filters, a common calibration method is to add liquid enzyme solution directly to the analysis cell, omitting the sampling and extraction stages altogether. As a result, the calibration does not accurately represent the uncertainties which are introduced in these processes. Using a system as above described, it is proposed that a suitably doped liquid is pipetted directly onto the filter 11 in order to load the device 300 with a known amount of enzyme. The remaining analysis steps can then be carried out as previously described, providing a calibration which at least takes some account of the relative efficiencies of both the absorption by the filter 11 and the subsequent extraction and reaction. The final output of the analysis instrument may then be calibrated in terms of enzyme mass loading, which is more useful to the user than optical density or some other analysis unit.

A typical housing in the form shown is approximately 109 mm in length. The housing is preferably made of polycarbonate, which offers a good combination of the robustness and optical clarity, although acrylic may be an alternative option. Polypropylene has been selected for the barrel section as this is known to be highly inert, is conventionally used in syringe components and is capable of containing aggressive reagents. Most of the minor parts are moulded in ABS, although other plastics could be used. A particular feature of the housing construction is that it has smooth internal surfaces, allowing free movement of the filter support 4 between the various different positions. Various seal materials may be employed, although injection-moulded thermoplastic elastomers (TPEs) are particularly appropriate. The filter 11 is approximately 24 mm in diameter and is preferably constructed of glass fibre material (e.g. Whatman GF/A, which is an industry standard filter).

It is envisaged that a sampling and analysis system could be provided for sampling of, for example, an industrial workplace. Each worker would be equipped with a sampling and analysis kit, comprising a device and holster assembly as described above and a pump, carried for example on the person's belt. The device 300 provides an integrated sampling, reaction and analysis vessel and, since its functions are automatically activated by mechanical interaction with the hardware (holster 15 and analyser), no external user actions are required. Importantly, no chemical or analytical skill is required to obtain reliable quantitative results.

A number of modifications to the above described apparatus are also envisaged. The cartridge could be designed so as to contain more than one analysis region, each provided with its own filter and reagent arrangement. Any combination of contaminants could be tested for, with appropriate chemistry and monitoring techniques provided for each.

A further possibility is the use of several chemistries in one cell so that more than one test can be facilitated in the same cartridge. In this respect it would be necessary to identify chemistries which do not interfere with one another and for which separate detection is possible.

Whilst the above description focusses on the industrial monitoring of protease enzymes (subtilisin in particular), there are a number of other airborne enzymes to which, with appropriate modification of the reaction chemistry, the same general approach may readily be applied. For example, cellulase, lipase and amylase are also used in detergent manufacture, and amylase is also widely employed in baking industries. A further important extension of the technique would be the analysis of fungi and bacteria which essentially comprise quantities of enzymes which may be released by appropriate reactions to attack the cell or spore casings. Analytes which are not enzymes could also be monitored by incorporating suitable chemical test reagents within the device. For example, the apparatus could be used to carry out immunoassays. The same device could even be used to monitor inorganic contaminants provided a suitable reaction could be identified, and appropriate reagents supplied.

One particular example is the use of the above described technique for airborne detection of mould spores. Here, the ease of use of the cartridge and its high integrity against contamination would be extremely beneficial. The chemistry employed in this application may however require a number of modifications to be made to the cartridge. In particular, the provision of several liquid reagents (released at appropriate points in the process), additional dry reagents and a waste collection region may be necessary. FIGS. 13 to 16 schematically illustrate suitable modifications.

Figure 13:
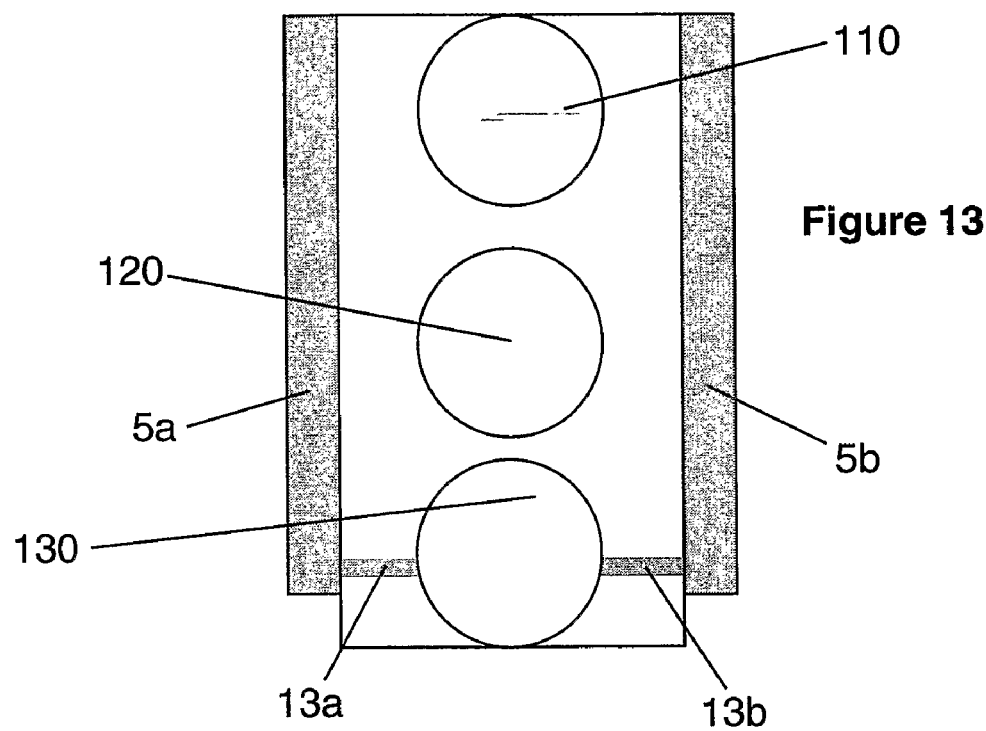
FIG. 13 is a schematic representation of a sampling and analysis device according to a second embodiment.

The cartridge could be provided with more than one reservoir region 5a, 5b and respective barrel/piston arrangements (FIG. 13). The multiple reservoirs or barrels could contain different reagents, and be released at the same or different times as required in appropriate volumes.

Figure 14A:
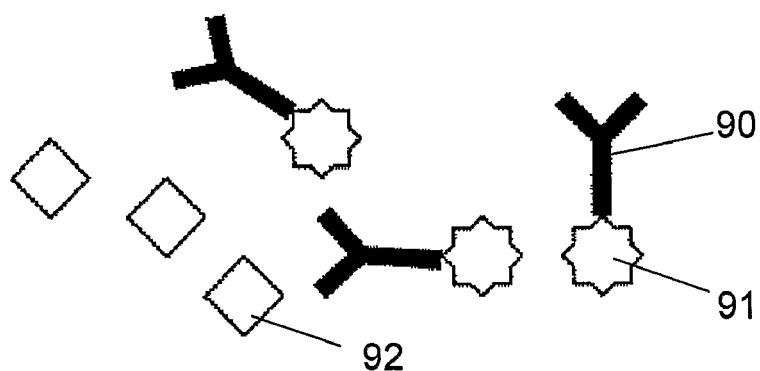
FIGS. 14a, 14b and 14c depict an immunoassay scheme.
Figure 14B:
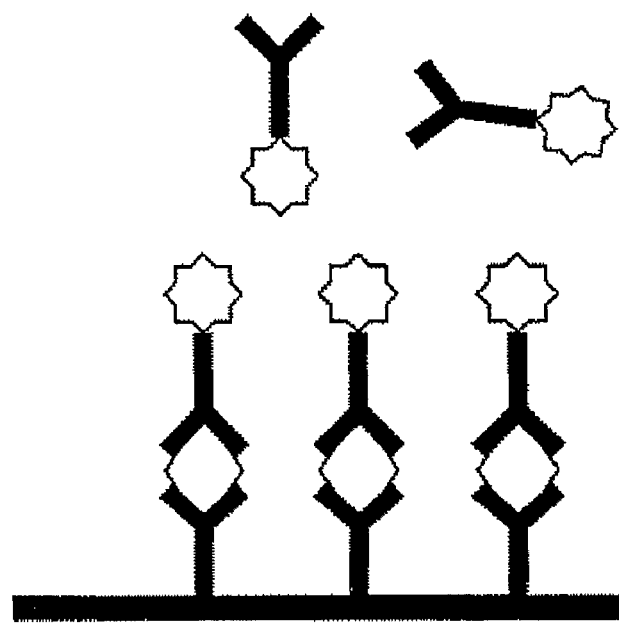
Figure 14C:
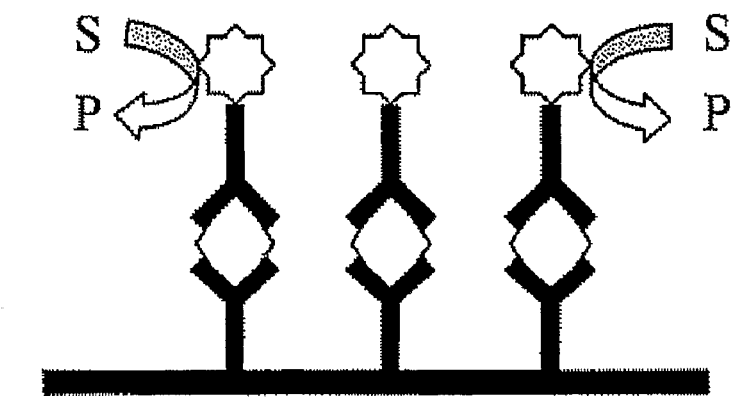

In an immunoassay sequence, the cartridge may need to accommodate several reagents and a washing step. FIGS. 14a, b and c depict a typical immunoassay scheme. Antibodies are represented as "Y"-shaped units 90 and 93, enzyme as stars 91 and analyte as diamonds 92. In an immunoassay the analyte is typically referred to as the antigen and is the component to which the antibody specifically bonds. FIG. 14a shows the first step in which liquid is released from a reservoir, dissolving a dry antibody 90 (already present in the analysis region) and releasing antigen 92 from the filter. The dissolved antibody 90 has enzyme 91 conjugated to it. Another antibody 93 is immobilised to a surface 94 within the analysis chamber. Binding is then allowed to take place for a chosen time. In the second step (shown in FIG. 14b), after binding, analyte 92 is bound to the immobilised antibody 93 and the enzyme labelled antibody 90 is bound to another site on the analyte 92. The quantitative event (to be monitored in the analyser) is that more enzyme 91 becomes immobilised if more analyte is present. The amount of immobilised enzyme 91 must be accurately determined as a measure of the original analyte. Any excess enzyme labelled antibody 90 needs to be washed away since otherwise the free enzyme would generate an erroneous signal. In step 3 (FIG. 14c), the immobilised enzyme is detected by presenting it with a substrate S and detecting the product P, as described above. A commonly used enzyme label is alkaline phosphatase, with nitrophenyl phosphate substrate (colourless) generating nitrophenol product (yellow) for spectrophotometric detection. Alternatively, fluorescent labels could be used.

Figure 15:
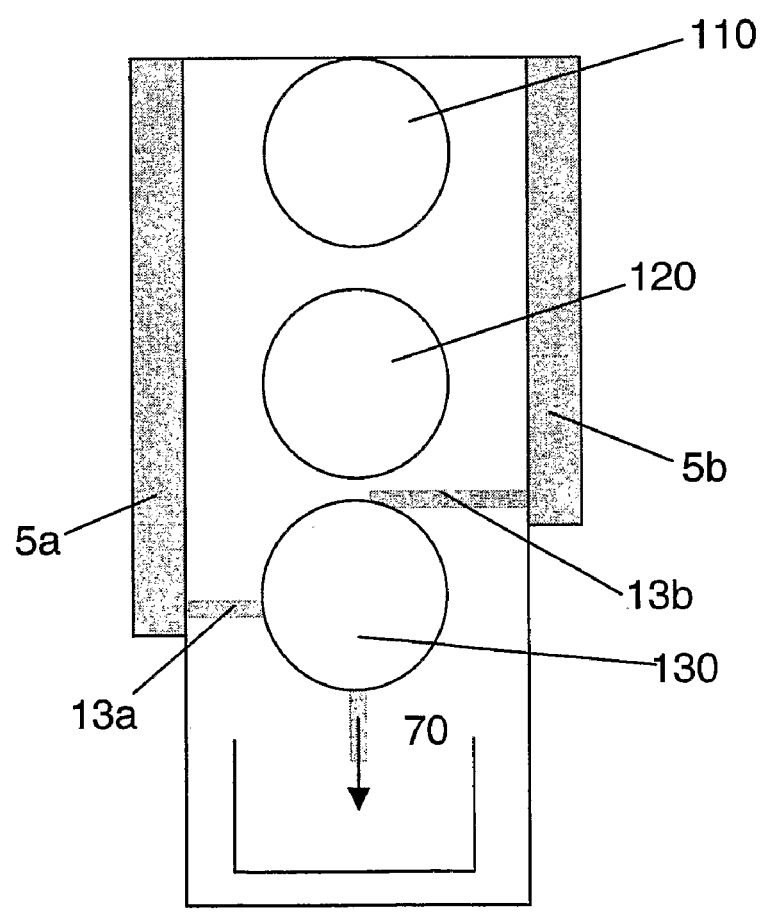
FIG. 15 is a schematic representation of a sampling and analysis device according to a third embodiment.

A waste receptacle 72 may need to be provided below the analysis chamber to collect waste during the washing step. FIG. 15 is a schematic diagram of a suitable cartridge configuration. In the first analysis step, a reagent mixture is released from a first reservoir region 5a to fill the analysis region. Additional reagent may be immobilised in dry form in the chamber, dissolving in the released liquid. There may be stirring to enhance the dissolution of the dry reagents and improve mixing. At an appropriate time, a second reagent is released from reservoir region 5b to rinse the analysis region. The entry port 13b from the second reservoir region 5b adjoins the top of the analysis region to assist in rinsing. Exit port 70 would be closed initially and during the first analysis step and then open during rinsing. The port 70 could be closed again for a detection step, in which extra reagents might be added from either reservoir region 5a or 5b, or from an additional reservoir (not shown).

Reagents in dry form in the analysis region can only be used in the first step. Any subsequent dried reagents would have to be positioned in a region that only gets wet when they are to be used; for example, a porous pad in one of the connecting passages between the reservoirs and the analysis region.

Figure 16:
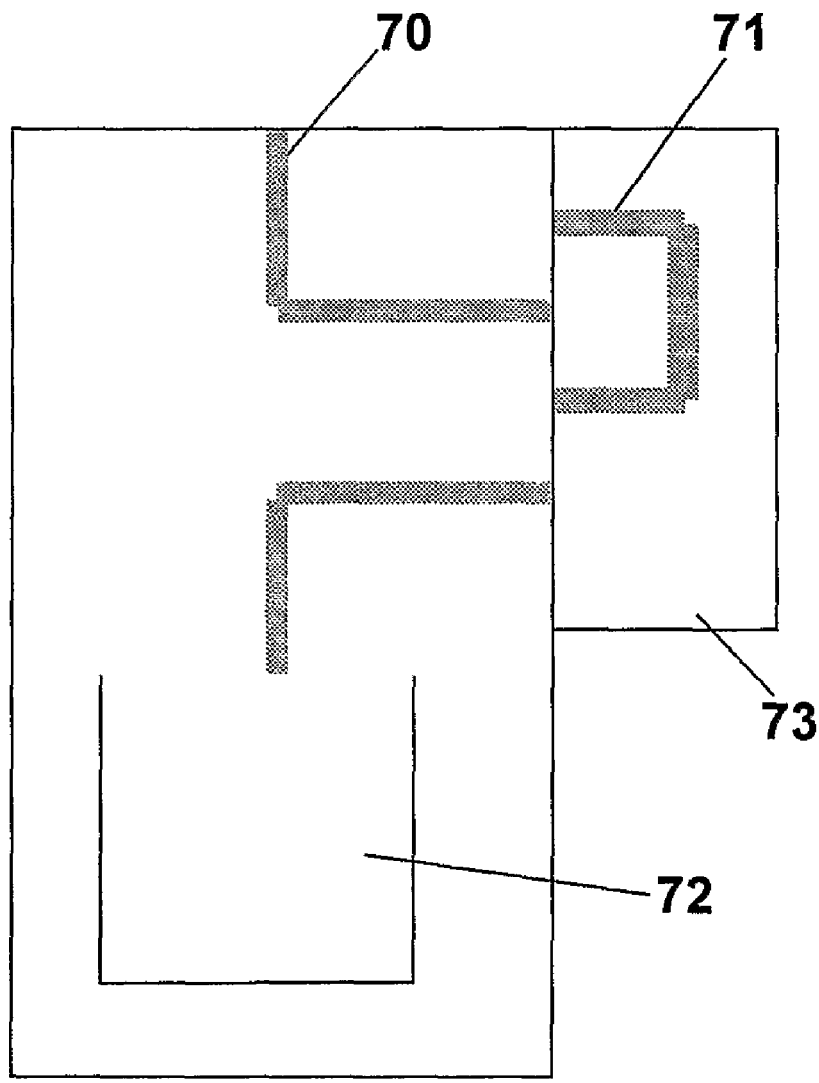
FIG. 16 is a schematic representation of a portion of the device shown in FIG. 15.

Exit port 70 could be configured as a piston valve to allow for controlled opening and closing. An exemplary arrangement is illustrated in FIG. 16. Exit port 70 is formed by a channel of which a portion 71 is located in a sliding piston 73. When the valve is closed, the portion 71 of exit port channel 70 does not align with the rest of the channel and as a result fluid cannot flow into waste receptacle 72. When a downward force is applied to sliding piston 73, the channels align and complete the path from the analysis region to waste receptacle 72. The liquid channel can thus be completed when required and blocked to stop the flow at a later time. Several such channel portions 71 provided on one piston 73 would enable several opening and closing sequences to take place under the application of a unidirectional force, interrupted at appropriate intervals to provide a sequence of valve actions.

A further embodiment envisaged is provided with an elongate strip (not shown) located at least partially in the analysis region 130 (referring to FIG. 1). During the analysis sequence, the filter comes into close proximity to a portion, preferably one end of, the elongate strip. Release of liquid or gel reagents into the analysis region transfers the collected sample to the strip which could be provided with a series of dried reagents. For example, the elongate strip could comprise a capillary strip incorporating a sequence of dried reagents for carrying out an immunoassay.

The collected sample, in solution, is drawn through the strip under capillary action and undergoes a series of reactions as it meets the dried reagents. This has the advantage of performing a whole analysis sequence without the need for a large number of liquid reagents or a complex control system to manage the sequence of steps. A single reagent release step can initiate any number of reactions, depending on the arrangement of dried reagents. The resulting reactions are predictable and can be monitored using conventional techniques. The device housing may be provided with additional analysis windows at appropriate points along the elongate strip through which certain stages of the sequence may be monitored.

The invention claimed is:

1. A sampling and analysis device comprising
a housing, a sampling region and an analysis region being defined within the housing, the housing having at least one aperture to allow fluid ingress to and egress from the sampling region; and
a filter cartridge disposed completely within the housing, wherein the filter cartridge is slidable along a rectilinear path inside the housing between a sampling position, located in the sampling region, and an analysis position, located in the analysis region.

2. A sampling and analysis device according to claim 1 further comprising means for introducing a reagent to the analysis region.

3. A sampling and analysis device according to claim 2 wherein the means for introducing a reagent comprise a reservoir adapted to contain a reagent in use, a passage between the reservoir and the analysis region and apparatus for causing the reagent to flow into the analysis region.

4. A sampling and analysis device according to claim 3 wherein the apparatus for causing the reagent to flow into the analysis region is a piston provided inside the reservoir.

5. A sampling and analysis device according to claim 2, wherein the housing is further provided with an analysis actuator aperture positioned away from the analysis region.

6. A sampling and analysis device according to claim 5 further comprising an analyser adapted to monitor conditions inside the device.

7. A sampling and analysis device according to claim 6 wherein the analyser is adapted to couple with the device in use, and comprises means for moving the filter cartridge inside the device housing.

8. A sampling and analysis device according to claim 7, wherein the means for moving the filter cartridge provided on the analyser comprise a shaft which can be inserted into the housing through the analysis actuation aperture to contact and apply a force to a filter support.

9. A sampling and analysis device according to claim 7, wherein the means for moving the filter cartridge provided on the analyser are adapted to move the filter cartridge from a safe position to the analysis position.

10. A sampling and analysis device according to claim 6, further comprising a reagent actuator for operating the means for introducing reagent to the analysis region of the device.

11. A sampling and analysis device according to claim 10, wherein the reagent actuator comprises a first actuator rod which cooperates with a piston provided inside a reservoir adapted to contain a reagent so as to force the reagent into the analysis region as the rod is moved relative to the device.

12. A sampling and analysis device according to claim 11 wherein the reagent actuator further comprises a second actuator rod which cooperates with the reservoir.

13. A sampling and analysis device according to claim 6, wherein the analyser is provided with means for optical interrogation of the contents of the analysis region.

14. A sampling and analysis device according to claim 6 wherein the analyser further comprises a stirrer actuator for operating a stirrer located in the analysis region.

15. A sampling and analysis device according to claim 14 wherein the stirrer actuator is magnetically coupled with the stirrer.

16. A sampling and analysis device according to claim 6 further comprising means for heating the analysis region of the device.

17. A sampling and analysis device according to claim 2 wherein the means for introducing a reagent comprise a cavity adapted to contain a reagent in use, the cavity having at least one wall in common with the analysis region, at least a portion of the wall being frangible.

18. A sampling and analysis device according to claim 1 further comprising an a reagent actuator for operating the means for introducing reagent to the analysis region of the device.

19. A sampling and analysis device according to claim 1 further comprising first sealing means which isolate the analysis region from the sampling region at least when the filter cartridge is at the analysis position.

20. A sampling and analysis device according to claim 19 wherein the filter cartridge is mounted on a filter support, the filter cartridge support shaped so as to allow fluid to pass through the filter cartridge, in use.

21. A sampling and analysis device according to claim 20 wherein the first sealing means comprise a seal provided between the filter support and the housing.

22. A sampling and analysis device according to claim 21 wherein the first sealing means are mounted on the filter support.

23. A sampling and analysis device according to claim 20 wherein the filter support and the housing are slidably engaged.

24. A sampling and analysis device according to claim 23 the housing is further provided with an elongate aperture and the filter support comprises a tab which extends toward the elongate aperture.

25. A sampling and analysis device according to claim 24 further comprising a holster adapted to couple with the device.

26. A sampling and analysis device assembly according to claim 25 wherein the holster comprises means for affixing the assembly to a user.

27. A sampling and analysis device according to claim 25 wherein the holster is provided with means for moving the filter cartridge inside the device housing.

28. A sampling and analysis device according to claim 27, wherein the means for moving the filter cartridge provided on the holster comprise a protrusion which cooperates with the tab on the filter support so as to slide the filter support alongside the elongate aperture as the device and holster are moved relative to one another.

29. A sampling and analysis device according to claim 27 wherein the means for moving the filter cartridge provided on the holster move the filter cartridge from a safe position to the sampling position as the device and the holster are coupled together, and return the filter cartridge to the safe position as the device and the holster are uncoupled.

30. A sampling and analysis device according to claim 25 wherein the holster is provided with an aperture which, in use, aligns with the aperture of the device, and a passage extending from the aperture to an outlet adapted to be connected, in use, to a pump.

31. A sampling and analysis device according to claim 25 comprising a pump for drawing fluid through the device.

32. A sampling and analysis device according to claim 31 further comprising a hose extending between the device and the pump.

33. A sampling and analysis device according to claim 1 wherein the filter cartridge is movable along a rectilinear path inside the housing between the sampling and analysis positions.

34. A sampling and analysis device according to claim 1 wherein the device further defines a safe region within the housing, the filter cartridge being further movable between the sampling or analysis positions and a safe position, located in the safe region, the filter cartridge being sealed from at least the sampling region when the filter cartridge is at the safe position.

35. A sampling and analysis device according to claim 34 wherein the filter cartridge is movable along a rectilinear path inside the housing between the sampling, analysis and safe positions.

36. A sampling and analysis device according to claim 34 wherein, when the filter cartridge is at the safe position, it is further sealed from the analysis region.

37. A sampling and analysis device according to claim 34 further comprising sealing means which, when the filter cartridge is in the sampling position, confine fluid flow to a volume of the sampling region defined by the second sealing means.

38. A sampling and analysis device according to claim 37 wherein the second sealing means isolate the filter cartridge from the rest of the device when the filter cartridge is in the safe position.

39. A sampling and analysis device according to claim 37 wherein the second sealing means comprise a seal extending around the perimeter of the filter cartridge between the filter cartridge and the housing.

40. A sampling and analysis device according claim 1 wherein the housing is further provided with a window located in a wall of the analysis region.

41. A sampling and analysis device according to claim 1 further comprising a stirrer located in the analysis region.

42. A sampling and analysis device according to claim 41 wherein the stirrer is adapted to be remotely actuated.

43. A sampling and analysis device according to claim 41 wherein the stirrer is located in a plane substantially parallel to that of the filter cartridge, and is rotatable about an axis perpendicular to the plane.

44. A sampling and analysis device according to claim 43 wherein the stirrer is spaced from the filter cartridge in use.

45. A sampling and analysis device according to claim 1 wherein the aperture in the sampling region comprises an inlet aperture through which fluid enters the device, and the device further comprises an outlet aperture in the sampling region through which fluid exits the device, the filter cartridge being located between the inlet and outlet apertures when it is in the sampling position, so as to collect contaminants from fluid flowing between the inlet and outlet apertures.

46. A sampling and analysis device according to claim 1, wherein the device is adapted to be carried by a user.

47. A method of sampling and analysing contaminants in a fluid comprising the steps of
   a) providing a filter cartridge disposed completely within a housing;
   b) passing the fluid through the filter cartridge, located at a sampling position inside the housing, such that a sample of the contaminants remain on the filter cartridge,
   c) slidably moving the filter cartridge along a rectilinear path to an analysis position located in an analysis region inside the housing, and in which a reaction occurs involving at least some of the contaminants on the filter cartridge; and
   d) monitoring the reaction.

48. A method according to claim 47 further comprising, before step (b), moving the filter cartridge from a safe position in the housing, at which the fluid cannot contact the filter cartridge, to the sampling position.

49. A method according to claim 47 further comprising, after step (b) and before step (c), moving the filter cartridge to a safe position in the housing, at which the fluid cannot contact the filter cartridge.

50. A method according to claim 47 wherein step (c) further comprises the step of initiating the reaction.

51. A method according to claim 50 wherein the reaction is initiated by introducing a reagent to the analysis region.

52. A method according to claim 51 wherein step (c) comprises the steps of
   c1) moving the filter cartridge to the analysis position;
   c2) sealing the analysis region so as to isolate it from the rest of the housing; and
   c3) introducing a reagent to the analysis region.

53. A method according to claim 51 wherein step (c) comprises the steps of
   c1) moving the filter cartridge to a location adjacent to the analysis position,
   c2) introducing the reagent to the analysis region
   c3) moving the filter cartridge into the analysis position, and
   c4) sealing the analysis region.

* * * * *